(12) United States Patent
Mandelboim et al.

(10) Patent No.: US 7,825,085 B2
(45) Date of Patent: Nov. 2, 2010

(54) FRAGMENTS OF NKP44 AND NKP46 FOR TARGETING VIRAL-INFECTED AND TUMOR CELLS

(75) Inventors: Ofer Mandelboim, Shoham (IL); Angel Porgador, Lehavia (IL)

(73) Assignees: Yissum Research Development Company of the Hebrew University of Jerusalem, Jerusalem (IL); Ben-Gurion University of the Negev Research and Development Authority, Beer-Sheva (IL)

( * ) Notice: Subject to any disclaimer, the term of this patent is extended or adjusted under 35 U.S.C. 154(b) by 854 days.

(21) Appl. No.: 10/562,735

(22) PCT Filed: Jun. 30, 2004

(86) PCT No.: PCT/IL2004/000583
§ 371 (c)(1),
(2), (4) Date: May 19, 2006

(87) PCT Pub. No.: WO2005/000086
PCT Pub. Date: Jan. 6, 2005

(65) Prior Publication Data
US 2007/0203054 A1    Aug. 30, 2007

Related U.S. Application Data

(60) Provisional application No. 60/483,107, filed on Jun. 30, 2003.

(51) Int. Cl.
*A61K 38/14* (2006.01)
*A61K 38/17* (2006.01)
*C07K 14/705* (2006.01)
*C07K 9/00* (2006.01)

(52) U.S. Cl. .......................... 514/8; 530/322; 530/324; 530/350

(58) Field of Classification Search .................. None
See application file for complete search history.

(56) References Cited

U.S. PATENT DOCUMENTS

| | | | |
|---|---|---|---|
| 5,019,368 | A | 5/1991 | Epstein |
| 5,134,075 | A | 7/1992 | Hellstrom |
| 5,171,665 | A | 12/1992 | Hellstrom |
| 5,196,337 | A | 3/1993 | Ochi |
| 5,204,095 | A | 4/1993 | Goodall |
| 5,643,759 | A | 7/1997 | Pfreundschuh |
| 5,882,626 | A | 3/1999 | Epstein |
| 5,965,132 | A | 10/1999 | Thorpe |
| 6,004,554 | A | 12/1999 | Thorpe |
| 6,017,514 | A | 1/2000 | Epstein |
| 6,071,491 | A | 6/2000 | Epstein |
| 6,342,221 | B1 | 1/2002 | Thorpe |
| 6,703,018 | B2 | 3/2004 | Jardieu |
| 6,719,971 | B1 | 4/2004 | Carter |
| 6,723,538 | B2 | 4/2004 | Mack |
| 2006/0165592 | A1 | 7/2006 | Mandelboim |

FOREIGN PATENT DOCUMENTS

| | | | |
|---|---|---|---|
| WO | 02/08287 | A2 | 1/2002 |
| WO | WO 02/08287 | * | 1/2002 |
| WO | 02/008287 | A3 | 12/2002 |
| WO | 2004/053054 | A2 | 6/2004 |
| WO | 2004/053054 | A3 | 10/2004 |

OTHER PUBLICATIONS

Cantoni et al, The Journal of Experimental Medicine, 1999, vol. 189, No. 5, pp. 787.*
Arnon et al., "The mechanisms controlling the recognition of tumor and virus infected cells by NKp46" Blood. 2004;103:664-672.
Biassoni et al, "Human natural killer cell receptors and co-receptors" Immunol Rev. 2001;181:203-214.
Cantoni et al., "NKp44, a triggering receptor involved in tumor cell lysis by activated human natural killer cells, is a novel member of the immunoglobulin superfamily" J Exp. Med. 1999;189(5), 787-796.
Costello et al., "Defective expression and function of natural killer cell-triggering receptors in patients with acute myeloid leukemia" Blood. 2002;99:3661-3667.
Dennissen, et al., "Large, tissue-regulated domain diversity of heparan sulfates demonstrated by phage display antibodies" J Biol Chem 2002;277:10982.
Lee et al., "Alteration of terminal glycosylation sequences on N-linked oligosaccharides of Chinese hamster ovary cells by expression of beta-galactoside alpha 2,6-sialyltransferase" J Biol Chem. 1989; 264:13848-13855.
Mandelboim et al., "Human CD16 as a lysis receptor mediating direct natural killer cell cytotoxicity" Proc Natl Acad Sci U.S.A. 1999;96:5640-5644.

(Continued)

*Primary Examiner* — Bridget E Bunner
*Assistant Examiner* — Fozia M Hamud
(74) *Attorney, Agent, or Firm* — Winston & Strawn LLP

(57) ABSTRACT

The present invention relates generally to peptides derived from the natural cytotoxicity receptors on natural killer (NK) cells and to antibodies against peptide epitopes on these receptors. In particular, the present invention identifies an essential epitope in the proximal domain of NKp46 and NKp44 receptors present on NK cells, as a crucial element for the binding to viral-infected cells. The present invention provides peptides that are derived from the amino acid sequence of NKp46 receptor, capable of specific targeting of viral-infected cells and tumor cells and monoclonal antibodies which recognize a specific domain of NKp46. The present invention further provides hyperglycosylated peptides that are derived from the NKp44 receptor, capable of specific targeting of viral-infected cells.

26 Claims, 12 Drawing Sheets

OTHER PUBLICATIONS

Mandelboim et al., "Recognition of haemagglutinins on virus-infected cells by NKp46 activates lysis by human NK cells" Nature. 2001;409:1055-1060.

Markel et al., "Pivotal role of CEACAM1 protein in the inhibition of activated decidual lymphocyte functions" J Clin Invest. 2002;110:943-953.

Pende et al., "Identification and molecular characterization of NKp30, a novel triggering receptor involved in natural cytotoxicity mediated by human natural killer cells" J Exp Med. 1999;190:1505-1516.

Pessino et al., "Molecular cloning of NKp46: a novel member of the immunoglobulin superfamily involved in triggering of natural cytotoxicity" J Exp Med. 1998;188:953-960.

Skehel et al., "Changes in the conformation of influenza virus hemagglutinin at the pH optimum of virus-mediated membrane fusion" Proc Natl Acad Sci U S A. 1982;79:968-972.

Sivori et al., "p46, A novel natural killer cell-specific surface molecule that mediates cell activation" J Exp Med. 1997;186:1129-1136.

Vankayalapati et al., "The NKp46 receptor contributes to NK cell lysis of mononuclear phagocytes infected with an intracellular bacterium" J Immunol. 2002;168:3451-3457.

Vitale et al., "NKp44, a novel triggering surface molecule specifically expressed by activated natural killer cells, is involved in non-major histocompatibility complex-restricted tumor cell lysis" J Exp Med. 1998;187:2065-2072.

* cited by examiner

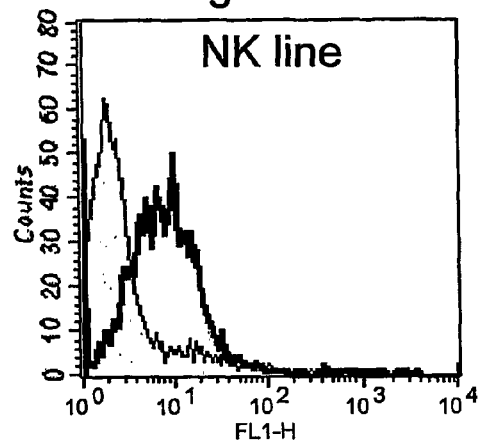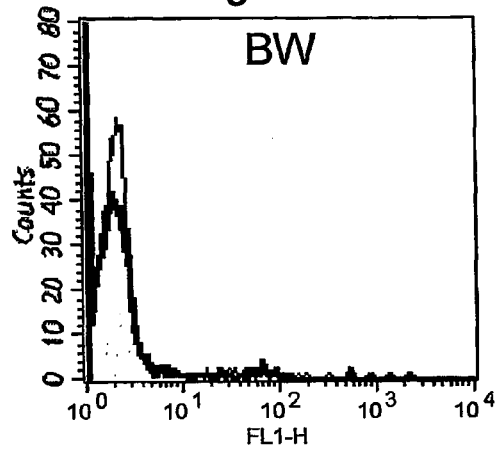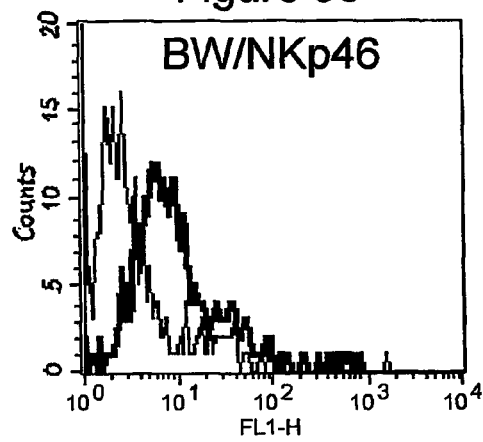

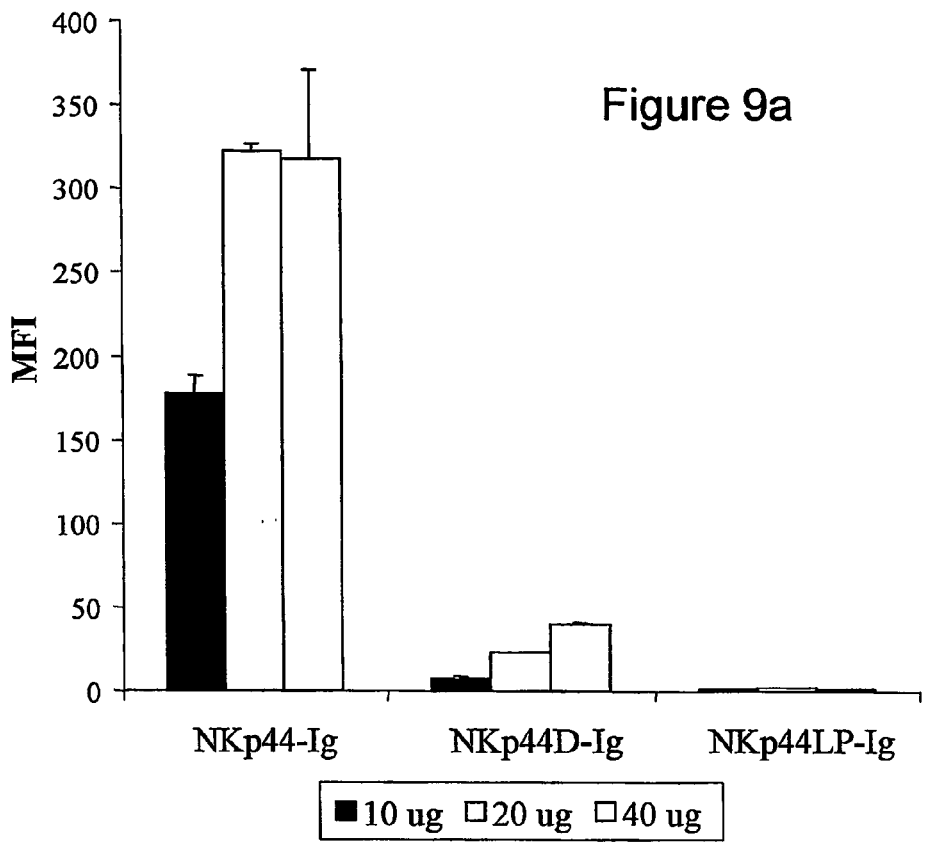
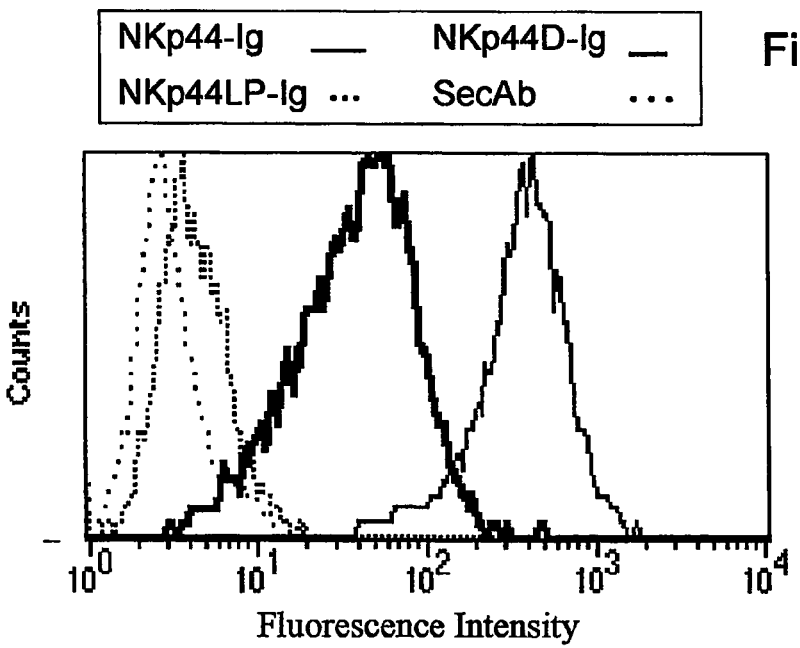

SEQUENCE LISTING

```
<160> NUMBER OF SEQ ID NOS: 21

<210> SEQ ID NO 1
<211> LENGTH: 304
<212> TYPE: PRT
<213> ORGANISM: Homo sapiens
<300> PUBLICATION INFORMATION:
<308> DATABASE ACCESSION NUMBER: CAA04714
<309> DATABASE ENTRY DATE: 1998-09-22
<313> RELEVANT RESIDUES: (1)..(304)

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Gln Thr Leu Pro Lys Pro Phe Ile Trp
                20                  25                  30

Ala Glu Pro His Phe Met Val Pro Lys Glu Lys Gln Val Thr Ile Cys
            35                  40                  45

Cys Gln Gly Asn Tyr Gly Ala Val Glu Tyr Gln Leu His Phe Glu Gly
        50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
```

```
                    85                  90                  95
Ser Cys Ile Tyr Arg Val Gly Glu Leu Trp Ser Glu Pro Ser Asn Leu
                100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
        130                 135                 140

Arg Leu Asp Thr Ala Thr Ser Met Phe Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
            260                 265                 270

Leu Val Glu Asp Trp Leu Ser Arg Lys Arg Thr Arg Glu Arg Ala Ser
        275                 280                 285

Arg Ala Ser Thr Trp Glu Gly Arg Arg Arg Leu Asn Thr Gln Thr Leu
    290                 295                 300

<210> SEQ ID NO 2
<211> LENGTH: 134
<212> TYPE: PRT
<213> ORGANISM: Homo sapiens
<220> FEATURE:
<221> NAME/KEY: PEPTIDE
<222> LOCATION: (1)..(134)
<223> OTHER INFORMATION: Residues 121-254 of SEQ ID NO:1

<400> SEQUENCE: 2

Tyr Asp Thr Pro Thr Leu Ser Val His Pro Gly Pro Glu Val Ile Ser
1               5                   10                  15

Gly Glu Lys Val Thr Phe Tyr Cys Arg Leu Asp Thr Ala Thr Ser Met
            20                  25                  30

Phe Leu Leu Lys Glu Gly Arg Ser Ser His Val Gln Arg Gly Tyr
        35                  40                  45

Gly Lys Val Gln Ala Glu Phe Pro Leu Gly Pro Val Thr Thr Ala His
    50                  55                  60

Arg Gly Thr Tyr Arg Cys Phe Gly Ser Tyr Asn Asn His Ala Trp Ser
65                  70                  75                  80

Phe Pro Ser Glu Pro Val Lys Leu Leu Val Thr Gly Asp Ile Glu Asn
                85                  90                  95

Thr Ser Leu Ala Pro Glu Asp Pro Thr Phe Pro Ala Asp Thr Trp Gly
            100                 105                 110

Thr Tyr Leu Leu Thr Thr Glu Thr Gly Leu Gln Lys Asp His Ala Leu
        115                 120                 125

Trp Asp His Thr Ala Gln
    130
```

```
<210> SEQ ID NO 3
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: Residues 215 to 254 of SEQ ID NO:1.

<400> SEQUENCE: 3

Glu Asn Thr Ser Leu Ala Pro Glu Asp Pro Thr Phe Pro Ala Asp Thr
1               5                   10                  15

Trp Gly Thr Tyr Leu Leu Thr Thr Glu Thr Gly Leu Gln Lys Asp His
            20                  25                  30

Ala Leu Trp Asp His Thr Ala Gln
        35                  40

<210> SEQ ID NO 4
<211> LENGTH: 258
<212> TYPE: PRT
<213> ORGANISM: Homo sapiens
<300> PUBLICATION INFORMATION:
<308> DATABASE ACCESSION NUMBER: CAC09453
<309> DATABASE ENTRY DATE: 2005-05-18
<313> RELEVANT RESIDUES: (1)..(258)

<400> SEQUENCE: 4

Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
            20                  25                  30

Gly Gln Thr Leu Thr Val Arg Cys Gln Tyr Pro Pro Thr Gly Ser Leu
        35                  40                  45

Tyr Glu Lys Lys Gly Trp Cys Lys Glu Ala Ser Ala Leu Val Cys Ile
    50                  55                  60

Arg Leu Val Thr Ser Ser Lys Pro Arg Thr Met Ala Trp Thr Ser Arg
65                  70                  75                  80

Phe Thr Ile Trp Asp Asp Pro Asp Ala Gly Phe Phe Thr Val Thr Met
                85                  90                  95

Thr Asp Leu Arg Glu Glu Asp Ser Gly His Tyr Trp Cys Arg Ile Tyr
            100                 105                 110

Arg Pro Ser Asp Asn Ser Val Ser Lys Ser Val Arg Phe Tyr Leu Val
        115                 120                 125

Val Ser Pro Ala Ser Ala Ser Thr Gln Thr Ser Trp Thr Pro Arg Asp
    130                 135                 140

Leu Val Ser Ser Gln Thr Gln Thr Gln Ser Cys Val Pro Pro Thr Ala
145                 150                 155                 160

Gly Ala Arg Gln Ala Pro Glu Ser Pro Ser Thr Ile Pro Val Pro Ser
                165                 170                 175

Gln Pro Gln Asn Ser Thr Leu Arg Pro Gly Pro Ala Ala Pro Ile Ala
            180                 185                 190

Leu Val Pro Val Phe Cys Gly Leu Leu Val Ala Lys Ser Leu Val Leu
        195                 200                 205

Ser Ala Leu Leu Val Trp Trp Val Leu Arg Asn Arg His Met Gln His
    210                 215                 220

Gln Gly Arg Ser Leu Leu His Pro Ala Gln Pro Arg Pro Gln Ala His
225                 230                 235                 240
```

```
Arg His Phe Pro Leu Ser His Arg Ala Pro Gly Gly Thr Tyr Gly Gly
                245                 250                 255

Lys Pro

<210> SEQ ID NO 5
<211> LENGTH: 114
<212> TYPE: PRT
<213> ORGANISM: Homo sapiens
<220> FEATURE:
<221> NAME/KEY: PEPTIDE
<222> LOCATION: (1)..(114)
<223> OTHER INFORMATION: residues 22-134 of SEQ ID NO:4

<400> SEQUENCE: 5

Gln Ser Lys Ala Gln Val Leu Gln Ser Val Ala Gly Gln Thr Leu Thr
1               5                   10                  15

Val Arg Cys Gln Tyr Pro Pro Thr Gly Ser Leu Tyr Glu Lys Lys Gly
            20                  25                  30

Trp Cys Lys Glu Ala Ser Ala Leu Val Cys Ile Arg Leu Val Thr Ser
        35                  40                  45

Ser Lys Pro Arg Thr Met Ala Trp Thr Ser Arg Phe Thr Ile Trp Asp
    50                  55                  60

Asp Pro Asp Ala Gly Phe Phe Thr Val Thr Met Thr Asp Leu Arg Glu
65                  70                  75                  80

Glu Asp Ser Gly His Tyr Trp Cys Arg Ile Tyr Arg Pro Ser Asp Asn
                85                  90                  95

Ser Val Ser Lys Ser Val Arg Phe Tyr Leu Val Val Ser Pro Ala Ser
            100                 105                 110

Ala Ser

<210> SEQ ID NO 6
<211> LENGTH: 55
<212> TYPE: PRT
<213> ORGANISM: Homo sapiens
<220> FEATURE:
<221> NAME/KEY: PEPTIDE
<222> LOCATION: (1)..(55)
<223> OTHER INFORMATION: residues 136-190 from SEQ ID NO:4

<400> SEQUENCE: 6

Thr Gln Thr Ser Trp Thr Pro Arg Asp Leu Val Ser Ser Gln Thr Gln
1               5                   10                  15

Thr Gln Ser Cys Val Pro Pro Thr Ala Gly Ala Arg Gln Ala Pro Glu
            20                  25                  30

Ser Pro Ser Thr Ile Pro Val Pro Ser Gln Pro Gln Asn Ser Thr Leu
        35                  40                  45

Arg Pro Gly Pro Ala Ala Pro
    50                  55

<210> SEQ ID NO 7
<211> LENGTH: 61
<212> TYPE: PRT
<213> ORGANISM: Homo sapiens
<220> FEATURE:
<221> NAME/KEY: PEPTIDE
<222> LOCATION: (1)..(61)
<223> OTHER INFORMATION: residues 109-169 of SEQ ID NO:4.

<400> SEQUENCE: 7

Ser Pro Ala Ser Ala Ser Thr Gln Thr Ser Trp Thr Pro Arg Asp Leu
1               5                   10                  15
```

```
Val Ser Ser Gln Thr Gln Thr Gln Ser Cys Val Pro Pro Thr Ala Gly
            20                  25                  30

Ala Arg Gln Ala Pro Glu Ser Pro Ser Thr Ile Pro Val Pro Ser Gln
            35                  40                  45

Pro Gln Asn Ser Thr Leu Arg Pro Gly Pro Ala Ala Pro
            50                  55                  60

<210> SEQ ID NO 8
<211> LENGTH: 99
<212> TYPE: PRT
<213> ORGANISM: Homo sapiens
<220> FEATURE:
<221> NAME/KEY: PEPTIDE
<222> LOCATION: (1)..(99)
<223> OTHER INFORMATION: residues 22-120 of SEQ ID NO:1 refered to as
      D1 domain

<400> SEQUENCE: 8

Gln Gln Gln Thr Leu Pro Lys Pro Phe Ile Trp Ala Glu Pro His Phe
 1               5                  10                  15

Met Val Pro Lys Glu Lys Gln Val Thr Ile Cys Cys Gln Gly Asn Tyr
            20                  25                  30

Gly Ala Val Glu Tyr Gln Leu His Phe Glu Gly Ser Leu Phe Ala Val
            35                  40                  45

Asp Arg Pro Lys Pro Pro Glu Arg Ile Asn Lys Val Lys Phe Tyr Ile
            50                  55                  60

Pro Asp Met Asn Ser Arg Met Ala Gly Gln Tyr Ser Cys Ile Tyr Arg
65                  70                  75                  80

Val Gly Glu Leu Trp Ser Glu Pro Ser Asn Leu Leu Asp Leu Val Val
                85                  90                  95

Thr Glu Met

<210> SEQ ID NO 9
<211> LENGTH: 30
<212> TYPE: DNA
<213> ORGANISM: Artificial
<220> FEATURE:
<223> OTHER INFORMATION: primer derived from human NKp44 nucleotide
      sequence
<220> FEATURE:
<221> NAME/KEY: misc_feature
<222> LOCATION: (1)..(30)
<223> OTHER INFORMATION: primer

<400> SEQUENCE: 9
ggcagggtac cccaatccaa ggctcaggta                                    30

<210> SEQ ID NO 10
<211> LENGTH: 30
<212> TYPE: DNA
<213> ORGANISM: Artificial
<220> FEATURE:
<223> OTHER INFORMATION: primer derived from human NKp44 nucleotide
      sequence

<400> SEQUENCE: 10
ggcagggtac cctctccagc ctctgcctcc                                    30

<210> SEQ ID NO 11
<211> LENGTH: 21
<212> TYPE: DNA
<213> ORGANISM: Homo sapiens

<400> SEQUENCE: 11
```

-continued

```
gccgtccacg taccagttga a                                          21
```

<210> SEQ ID NO 12
<211> LENGTH: 25
<212> TYPE: DNA
<213> ORGANISM: Artificial
<220> FEATURE:
<223> OTHER INFORMATION: primer derived from human NKp44 nucleotide
      sequence

<400> SEQUENCE: 12

```
aaggatccgc tggagatacc accag                                      25
```

<210> SEQ ID NO 13
<211> LENGTH: 488
<212> TYPE: PRT
<213> ORGANISM: Homo sapiens
<300> PUBLICATION INFORMATION:
<302> TITLE: NK Cells Activating Receptors and their Therapeutic and
      Diagnostic Uses
<310> PATENT DOCUMENT NUMBER: WO0208287
<311> PATENT FILING DATE: 2001-07-19
<312> PUBLICATION DATE: 2002-01-31
<313> RELEVANT RESIDUES: (1)..(488)

<400> SEQUENCE: 13

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
        115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asp Pro
                245                 250                 255
```

```
Glu Pro Lys Ser Ser Asp Lys Thr His Thr Cys Pro Cys Pro Ala
            260                 265                 270

Pro Glu Phe Glu Gly Ala Pro Ser Val Phe Leu Phe Pro Pro Lys Pro
        275                 280                 285

Lys Asp Thr Leu Met Ile Ser Arg Thr Pro Glu Val Thr Cys Val Val
            290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
        450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 14
<211> LENGTH: 364
<212> TYPE: PRT
<213> ORGANISM: Homo sapiens
<300> PUBLICATION INFORMATION:
<302> TITLE: NK Cells Activating Receptors and their Therapeutic and
      Diagnostic Uses
<310> PATENT DOCUMENT NUMBER: WO0208287
<311> PATENT FILING DATE: 2001-07-19
<312> PUBLICATION DATE: 2002-01-31
<313> RELEVANT RESIDUES: (1)..(364)

<400> SEQUENCE: 14

Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Gln
            20                  25                  30

Gln Gln Thr Leu Pro Lys Pro Phe Ile Trp Ala Glu Pro His Phe Met
        35                  40                  45

Val Pro Lys Glu Lys Gln Val Thr Ile Cys Cys Gln Gly Asn Tyr Gly
    50                  55                  60

Ala Val Glu Tyr Gln Leu His Phe Glu Gly Ser Leu Phe Ala Val Asp
65                  70                  75                  80

Arg Pro Lys Pro Pro Glu Arg Ile Asn Lys Val Lys Phe Tyr Ile Pro
                85                  90                  95

Asp Met Asn Ser Arg Met Ala Gly Gln Tyr Ser Cys Ile Tyr Arg Val
```

-continued

```
            100                 105                 110
Gly Glu Leu Trp Ser Glu Pro Ser Asn Leu Leu Asp Leu Val Val Thr
            115                 120                 125

Glu Met Asp Pro Glu Pro Lys Ser Ser Asp Lys Thr His Thr Cys Pro
        130                 135                 140

Pro Cys Pro Ala Pro Glu Phe Glu Gly Ala Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360
```

<210> SEQ ID NO 15
<211> LENGTH: 393
<212> TYPE: PRT
<213> ORGANISM: Homo sapiens

<400> SEQUENCE: 15

```
Met Gly Met Pro Met Gly Ser Leu Gln Pro Leu Ala Thr Leu Tyr Leu
1               5                   10                  15

Leu Gly Met Leu Val Ala Ser Cys Leu Gly Arg Leu Arg Val Pro Tyr
                20                  25                  30

Asp Thr Pro Thr Leu Ser Val His Pro Gly Pro Glu Val Ile Ser Gly
            35                  40                  45

Glu Lys Val Thr Phe Tyr Cys Arg Leu Asp Thr Ala Thr Ser Met Phe
        50                  55                  60

Leu Leu Leu Lys Glu Gly Arg Ser Ser His Val Gln Arg Gly Tyr Gly
65                  70                  75                  80

Lys Val Gln Ala Glu Phe Pro Leu Gly Pro Val Thr Thr Ala His Arg
                85                  90                  95

Gly Thr Tyr Arg Cys Phe Gly Ser Tyr Asn Asn His Ala Trp Ser Phe
            100                 105                 110
```

-continued

```
Pro Ser Glu Pro Val Lys Leu Leu Val Thr Gly Asp Ile Glu Asn Thr
            115                 120                 125
Ser Leu Ala Pro Glu Asp Pro Thr Phe Pro Asp Thr Trp Gly Thr Tyr
        130                 135                 140
Leu Leu Thr Thr Glu Thr Gly Leu Gln Lys Asp His Ala Leu Trp Asp
145                 150                 155                 160
Pro Glu Pro Lys Ser Ser Asp Lys Thr His Thr Cys Pro Pro Cys Pro
                165                 170                 175
Ala Pro Glu Phe Glu Gly Ala Pro Ser Val Phe Leu Phe Pro Pro Lys
            180                 185                 190
Pro Lys Asp Thr Leu Met Ile Ser Arg Thr Pro Glu Val Thr Cys Val
        195                 200                 205
Val Val Asp Val Ser His Glu Asp Pro Glu Val Lys Phe Asn Trp Tyr
210                 215                 220
Val Asp Gly Val Glu Val His Asn Ala Lys Thr Lys Pro Arg Glu Glu
225                 230                 235                 240
Gln Tyr Asn Ser Thr Tyr Arg Val Val Ser Val Leu Thr Val Leu His
                245                 250                 255
Gln Asp Trp Leu Asn Gly Lys Glu Tyr Lys Cys Lys Val Ser Asn Lys
            260                 265                 270
Ala Leu Pro Ala Pro Ile Glu Lys Thr Ile Ser Lys Ala Lys Gly Gln
        275                 280                 285
Pro Arg Glu Pro Gln Val Tyr Thr Leu Pro Pro Ser Arg Asp Glu Leu
    290                 295                 300
Thr Lys Asn Gln Val Ser Leu Thr Cys Leu Val Lys Gly Phe Tyr Pro
305                 310                 315                 320
Ser Asp Ile Ala Val Glu Trp Glu Ser Asn Gly Gln Pro Glu Asn Asn
                325                 330                 335
Tyr Lys Thr Thr Pro Pro Val Leu Asp Ser Asp Gly Ser Phe Phe Leu
            340                 345                 350
Tyr Ser Lys Leu Thr Val Asp Lys Ser Arg Trp Gln Gln Gly Asn Val
        355                 360                 365
Phe Ser Cys Ser Val Met His Glu Ala Leu His Asn His Tyr Thr Gln
    370                 375                 380
Lys Ser Leu Ser Leu Ser Pro Gly Lys
385                 390
```

<210> SEQ ID NO 16
<211> LENGTH: 434
<212> TYPE: PRT
<213> ORGANISM: Homo sapiens
<300> PUBLICATION INFORMATION:
<302> TITLE: NK Cells Activating Receptors and their Therapeutic and
      Diagnostic Uses
<310> PATENT DOCUMENT NUMBER: WO0208287
<311> PATENT FILING DATE: 2001-07-19
<312> PUBLICATION DATE: 2002-01-31
<313> RELEVANT RESIDUES: (1)..(434)

<400> SEQUENCE: 16

```
Met Gly Met Pro Met Gly Ser Leu Gln Pro Leu Ala Thr Leu Tyr Leu
1               5                   10                  15
Leu Gly Met Leu Val Ala Ser Cys Leu Gly Arg Leu Arg Val Pro Gln
            20                  25                  30
Ser Lys Ala Gln Val Leu Gln Ser Val Ala Gly Gln Thr Leu Thr Val
        35                  40                  45
Arg Cys Gln Tyr Pro Pro Thr Gly Ser Leu Tyr Glu Lys Lys Gly Trp
```

```
                50                  55                  60
Cys Lys Glu Ala Ser Ala Leu Val Cys Ile Arg Leu Val Thr Ser Ser
 65                  70                  75                  80

Lys Pro Arg Thr Val Ala Trp Thr Ser Arg Phe Thr Ile Trp Asp Asp
                 85                  90                  95

Pro Asp Ala Gly Phe Phe Thr Val Thr Met Thr Asp Leu Arg Glu Glu
                100                 105                 110

Asp Ser Gly His Tyr Trp Cys Arg Ile Tyr Arg Pro Ser Asp Asn Ser
                115                 120                 125

Val Ser Lys Ser Val Arg Phe Tyr Leu Val Val Ser Pro Ala Ser Ala
            130                 135                 140

Ser Thr Gln Thr Ser Trp Thr Pro Arg Asp Leu Val Ser Ser Gln Thr
145                 150                 155                 160

Gln Thr Gln Ser Cys Val Pro Pro Thr Ala Gly Ala Arg Gln Ala Pro
                165                 170                 175

Glu Ser Pro Ser Thr Ile Pro Val Pro Ser Gln Pro Gln Asn Ser Thr
                180                 185                 190

Leu Arg Pro Gly Pro Ala Ala Pro Asp Pro Glu Pro Lys Ser Ser Asp
            195                 200                 205

Lys Thr His Thr Cys Pro Pro Cys Pro Ala Pro Glu Phe Glu Gly Ala
            210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Glu Val Lys Phe Asn Trp Tyr Val Asp Gly Val Glu Val His
                260                 265                 270

Asn Ala Lys Thr Lys Pro Arg Glu Glu Gln Tyr Asn Ser Thr Tyr Arg
            275                 280                 285

Val Val Ser Val Leu Thr Val Leu His Gln Asp Trp Leu Asn Gly Lys
            290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Asp Glu Leu Thr Lys Asn Gln Val Ser Leu
                340                 345                 350

Thr Cys Leu Val Lys Gly Phe Tyr Pro Ser Asp Ile Ala Val Glu Trp
            355                 360                 365

Glu Ser Asn Gly Gln Pro Glu Asn Asn Tyr Lys Thr Thr Pro Pro Val
            370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys

<210> SEQ ID NO 17
<211> LENGTH: 326
<212> TYPE: PRT
<213> ORGANISM: Homo sapiens
```

-continued

```
<400> SEQUENCE: 17

Met Gly Met Pro Met Gly Ser Leu Gln Pro Leu Ala Thr Leu Tyr Leu
 1               5                  10                  15

Leu Gly Met Leu Val Ala Ser Cys Leu Gly Arg Leu Arg Val Pro Ser
            20                  25                  30

Pro Ala Ser Ala Ser Thr Gln Thr Ser Trp Thr Pro Arg Asp Leu Val
        35                  40                  45

Ser Ser Gln Thr Gln Thr Gln Ser Cys Val Pro Pro Thr Ala Gly Ala
50                  55                  60

Arg Gln Ala Pro Glu Ser Pro Ser Thr Ile Pro Val Pro Ser Gln Pro
65                  70                  75                  80

Gln Asn Ser Thr Leu Arg Pro Gly Pro Ala Ala Pro Asp Pro Glu Pro
                85                  90                  95

Lys Ser Ser Asp Lys Thr His Thr Cys Pro Pro Cys Pro Ala Pro Glu
            100                 105                 110

Phe Glu Gly Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 18
<211> LENGTH: 376
<212> TYPE: PRT
<213> ORGANISM: Homo sapiens
<300> PUBLICATION INFORMATION:
<302> TITLE: NK Cells Activating Receptors and their Therapeutic and
      Diagnostic Uses
<310> PATENT DOCUMENT NUMBER: WO0208287
<311> PATENT FILING DATE: 2001-07-19
<312> PUBLICATION DATE: 2002-01-31
<313> RELEVANT RESIDUES: (1)..(376)

<400> SEQUENCE: 18
```

```
Met Gly Met Pro Met Gly Ser Phe Gln Pro Leu Ala Thr Leu Tyr Leu
 1               5                   10                  15

Leu Gly Met Leu Val Ala Ser Cys Leu Gly Arg Leu Arg Val Pro Gln
                20                  25                  30

Ser Lys Ala Gln Val Leu Gln Ser Val Ala Gly Gln Thr Leu Thr Val
            35                  40                  45

Arg Cys Gln Tyr Pro Pro Thr Gly Ser Leu Tyr Glu Lys Lys Gly Trp
 50                  55                  60

Cys Lys Glu Ala Ser Ala Leu Val Cys Ile Arg Leu Val Thr Ser Ser
 65                  70                  75                  80

Lys Pro Arg Thr Val Ala Trp Thr Ser Arg Phe Thr Ile Trp Asp Asp
                85                  90                  95

Pro Asp Ala Gly Phe Phe Thr Val Thr Met Thr Asp Leu Arg Glu Glu
                100                 105                 110

Asp Ser Gly His Tyr Trp Cys Arg Ile Tyr Arg Pro Ser Asp Asn Ser
            115                 120                 125

Val Ser Lys Ser Val Arg Phe Tyr Leu Val Val Ser Pro Ala Asp Pro
130                 135                 140

Glu Pro Lys Ser Ser Asp Lys Thr His Thr Cys Pro Pro Cys Pro Ala
145                 150                 155                 160

Pro Glu Phe Glu Gly Ala Pro Ser Val Phe Leu Phe Pro Pro Lys Pro
                165                 170                 175

Lys Asp Thr Leu Met Ile Ser Arg Thr Pro Glu Val Thr Cys Val Val
                180                 185                 190

Val Asp Val Ser His Glu Asp Pro Glu Val Lys Phe Asn Trp Tyr Val
            195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
                260                 265                 270

Arg Glu Pro Gln Val Tyr Thr Leu Pro Pro Ser Arg Asp Glu Leu Thr
            275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
                340                 345                 350

Ser Cys Ser Val Met His Glu Ala Leu His Asn His Tyr Thr Gln Lys
            355                 360                 365

Ser Leu Ser Leu Ser Pro Gly Lys
370                 375

<210> SEQ ID NO 19
<211> LENGTH: 287
<212> TYPE: PRT
<213> ORGANISM: Homo sapiens
<300> PUBLICATION INFORMATION:
```

<308> DATABASE ACCESSION NUMBER: CAA06872
<309> DATABASE ENTRY DATE: 1998-09-22
<313> RELEVANT RESIDUES: (1)..(287)

<400> SEQUENCE: 19

```
Met Ser Ser Thr Leu Pro Ala Leu Leu Cys Val Gly Leu Cys Leu Ser
1               5                   10                  15

Gln Arg Ile Ser Ala Gln Gln Gln Thr Leu Pro Lys Pro Phe Ile Trp
            20                  25                  30

Ala Glu Pro His Phe Met Val Pro Lys Glu Lys Gln Val Thr Ile Cys
        35                  40                  45

Cys Gln Gly Asn Tyr Gly Ala Val Glu Tyr Gln Leu His Phe Glu Gly
    50                  55                  60

Ser Leu Phe Ala Val Asp Arg Pro Lys Pro Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
        115                 120                 125

His Pro Gly Pro Glu Val Ile Ser Gly Glu Lys Val Thr Phe Tyr Cys
    130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
        195                 200                 205

Leu Val Thr Gly Asp Ile Glu Asn Thr Ser Leu Ala Pro Glu Asp Pro
    210                 215                 220

Thr Phe Pro Asp His Ala Leu Trp Asp His Thr Ala Gln Asn Leu Leu
225                 230                 235                 240

Arg Met Gly Leu Ala Phe Leu Val Leu Val Ala Leu Val Trp Phe Leu
                245                 250                 255

Val Glu Asp Trp Leu Ser Arg Lys Arg Thr Arg Glu Arg Ala Ser Arg
            260                 265                 270

Ala Ser Thr Trp Glu Gly Arg Arg Leu Asn Thr Gln Thr Leu
        275                 280                 285
```

<210> SEQ ID NO 20
<211> LENGTH: 209
<212> TYPE: PRT
<213> ORGANISM: Homo sapiens
<300> PUBLICATION INFORMATION:
<308> DATABASE ACCESSION NUMBER: CAA06873
<309> DATABASE ENTRY DATE: 2005-04-15
<313> RELEVANT RESIDUES: (1)..(209)

<400> SEQUENCE: 20

```
Met Ser Ser Thr Leu Pro Ala Leu Leu Cys Val Gly Leu Cys Leu Ser
1               5                   10                  15

Gln Arg Ile Ser Ala Gln Gln Gln Met Tyr Asp Thr Pro Thr Leu Ser
            20                  25                  30

Val His Pro Gly Pro Glu Val Ile Ser Gly Glu Lys Val Thr Phe Tyr
```

-continued

```
                 35                  40                  45
Cys Arg Leu Asp Thr Ala Thr Ser Met Phe Leu Leu Lys Glu Gly
         50                  55                  60

Arg Ser Ser His Val Gln Arg Gly Tyr Gly Lys Val Gln Ala Glu Phe
 65                  70                  75                  80

Pro Leu Gly Pro Val Thr Thr Ala His Arg Gly Thr Tyr Arg Cys Phe
                 85                  90                  95

Gly Ser Tyr Asn Asn His Ala Trp Ser Phe Pro Ser Glu Pro Val Lys
                100                 105                 110

Leu Leu Val Thr Gly Asp Ile Glu Asn Thr Ser Leu Ala Pro Glu Asp
            115                 120                 125

Pro Thr Phe Pro Ala Asp Thr Trp Gly Thr Tyr Leu Leu Thr Thr Glu
        130                 135                 140

Thr Gly Leu Gln Lys Asp His Ala Leu Trp Asp His Thr Ala Gln Asn
145                 150                 155                 160

Leu Leu Arg Met Gly Leu Ala Phe Leu Val Leu Val Ala Leu Val Trp
                165                 170                 175

Phe Leu Val Glu Asp Trp Leu Ser Arg Lys Arg Thr Arg Glu Arg Ala
            180                 185                 190

Ser Arg Ala Ser Thr Trp Glu Gly Arg Arg Arg Leu Asn Thr Gln Thr
        195                 200                 205

Leu
```

<210> SEQ ID NO 21
<211> LENGTH: 192
<212> TYPE: PRT
<213> ORGANISM: Homo sapiens
<300> PUBLICATION INFORMATION:
<308> DATABASE ACCESSION NUMBER: CAA06874
<309> DATABASE ENTRY DATE: 1998-09-22
<313> RELEVANT RESIDUES: (1)..(192)

<400> SEQUENCE: 21

```
Met Ser Ser Thr Leu Pro Ala Leu Leu Cys Val Gly Leu Cys Leu Ser
 1               5                  10                  15

Gln Arg Ile Ser Ala Gln Gln Met Tyr Asp Thr Pro Thr Leu Ser
            20                  25                  30

Val His Pro Gly Pro Glu Val Ile Ser Gly Glu Lys Val Thr Phe Tyr
        35                  40                  45

Cys Arg Leu Asp Thr Ala Thr Ser Met Phe Leu Leu Lys Glu Gly
         50                  55                  60

Arg Ser Ser His Val Gln Arg Gly Tyr Gly Lys Val Gln Ala Glu Phe
 65                  70                  75                  80

Pro Leu Gly Pro Val Thr Thr Ala His Arg Gly Thr Tyr Arg Cys Phe
                 85                  90                  95

Gly Ser Tyr Asn Asn His Ala Trp Ser Phe Pro Ser Glu Pro Val Lys
                100                 105                 110

Leu Leu Val Thr Gly Asp Ile Glu Asn Thr Ser Leu Ala Pro Glu Asp
            115                 120                 125

Pro Thr Phe Pro Asp His Ala Leu Trp Asp His Thr Ala Gln Asn Leu
        130                 135                 140

Leu Arg Met Gly Leu Ala Phe Leu Val Leu Val Ala Leu Val Trp Phe
145                 150                 155                 160

Leu Val Glu Asp Trp Leu Ser Arg Lys Arg Thr Arg Glu Arg Ala Ser
                165                 170                 175
```

```
                    -continued
Arg Ala Ser Thr Trp Glu Gly Arg Arg Arg Leu Asn Thr Gln Thr Leu
        180                 185                 190
```

FRAGMENTS OF NKP44 AND NKP46 FOR TARGETING VIRAL-INFECTED AND TUMOR CELLS

CROSS REFERENCE TO RELATED APPLICATIONS

This application is a 35 U.S.C. §371 filing of International Application No. PCT/IL2004/000583, filed Jun. 30, 2004 and published in English as WO 2005/000086 on Jan. 6, 2005; which claims the benefit of U.S. Provisional Application No. 60/483,107 filed Jun. 30, 2003, which applications are incorporated herein by reference in their entirety for all purposes.

FIELD OF THE INVENTION

The present invention relates generally to peptide fragments derived from the NKp46 and NKp44 receptors expressed on natural killer (NK) cells and to antibodies directed against epitopes on these receptors. In particular, the present invention identifies peptide sequences that are glycosylated or hyperglycosylated as crucial elements for the binding of the NK receptors to tumor cells and/or viral-infected cells. The present invention further provides fission proteins and synthetic peptides that are derived from the amino acid sequence of NKp46 receptor and NKp44 receptor, capable of specific binding to viral-infected cells and/or tumor cells.

BACKGROUND OF THE INVENTION

Natural killer (NK) cells are bone marrow derived lymphocytes that constitute a key frontline defense against a range of hazardous conditions including viral infection and tumor transformation[1]. Although NK cells can kill target cells spontaneously without prior stimulation, a delicate balance between inhibitory and activating signals tightly regulates their activation. NK cells express a family of inhibitory and activating receptors that recognize major histocompatibility complex (MHC) class I molecules[1]. Engagement of these receptors results in the transduction of inhibitory signals that, under normal physiological conditions, predominate over those mediated via activating receptors[1]. This insures that healthy cells, expressing adequate amounts of MHC class I, will be protected from NK cells attack, while cells that have lost normal expression of MHC class I molecules, often resulting from viral infection or cell transformation, will be destroyed[2].

This concept, however, accounts only in part for the regulation of activation, and non-MHC ligands also control NK-mediated killing[3]. In addition, certain NK-susceptible target cells express normal MHC class I repertoire, while some MHC-negative cells are resistant to NK attack[4]. It has now become evident that activation of NK cells requires more than just the absence of inhibitory signals and that in order to tip the balance in favor of NK cells activation, target cells must express ligands specific for activating receptors.

A significant breakthrough in the understanding of specific activation of NK cells was achieved following the recent identification of three novel NK specific triggering receptors collectively termed natural cytotoxic receptors (NCR). The NCRs, which include NKp46, NKp44 and NKp30, belong to the Ig superfamily but share no homology with each other and only a low degree of identity with any known human molecules[5,6,7]. Upon engagement, NCRs transduce activating signals through the association with various adaptor molecules (including the DAP12 and zeta chain proteins) that carry immunoreceptor tyrosine-based activation motifs (ITAM) in their cytoplasmatic tail, allowing activation via the src-kinase and syc-signaling pathway[5,7,8]. All of these NCRs are capable of mediating direct killing of tumor and virus-infected cells and are specific for non-MHC ligands. NKp46 and NKp30 are present exclusively on NK cells, whether resting or activated, while NKp44 is expressed specifically on activated NK cells.

The most distinctive role of the NCRs in NK cells activity has been attributed to their involvement in recognition and killing of tumor cells. This has become evident by the ability of anti-NCR monoclonal antibodies to block NK-mediated killing of most tumor lines[4-7,9] and by the strict correlation that exists between the density of NCRs expression on NK cells and their ability to kill tumor targets[9]. More recently, the importance of NCRs in vivo was illustrated in acute myeloid leukemia (AML) patients expressing insufficient amount of either NCR or NCR ligands, thereby rendering the leukemia cells resistant to NK cytotoxicity[10].

While NCRs have been implicated most conclusively in immunity against transformed cells, there is evidence they may also contribute to defense against pathogens[1,2,11,12]. This notion is supported by the fact that NK deficient individuals suffer from a range of recurrent diseases, especially viral infections[12]. Recently, the inventors and coworkers have demonstrated that soluble NKp46- and NKp44-immunoglobulin (Ig) fusion proteins, but not an NKp30-Ig fusion protein, specifically bind to hemagglutinin of influenza virus and to hemagglutinin-neuraminidase of Sendai virus[13-15]. This interaction is functional and can mediate an enhanced killing of infected cells. This enhanced killing can be abolished by antibodies that block either the HA or the lysis receptors NKp46 and NKp44[13-15].

The human NKp46 receptor has multiple isoforms including the currently known isoforms: Isoform a (Accession No CAA04714; SEQ ID NO:1); Isoform b (Accession No. CAA06872) Isoform c (Accession No. CAA06873) Isoform d (Accession No. CAA06874). In general the NKp46 receptor comprises two extracellular Ig-like domains of the C2 type, a transmembrane portion and an intracellular segment. The extracellular portion of NKp46 comprises a D1 domain, designated NKp46D1 (comprising residues 22-120 of the mature full length protein of isoform a) a D2 domain, designated NKp46D2, comprising 134 amino acid residues (residues 121-254 of the full length receptor of isoform a; SEQ ID NO:2).

The human NKp44 receptor (accession No CAC09453; SEQ ID NO:4) comprises one extracellular portion designated herein NKp44D (residues 22-135 of the full length receptor; SEQ ID NO:5), comprising a single globular domain and a tail (residues 136-190).

WO 02/08287 of the present inventors discloses NK receptor fusion proteins in which the extracellular portion of the various NK receptors is conjugated to an active segment comprising an immunoglobulin (Ig), a cytotoxic moiety or an imaging moiety. WO 02/08287 further discloses that the NK receptor fusion proteins exhibit specific interaction with tumor cells and viral-infected cells in vitro.

There is an unmet need for characterization of the molecular features or epitopes involved in killing of viral infected and tumor cells. The present invention discloses peptides derived from the amino acid sequences of NKp44 and NKp46, and essential epitopes therein that are crucial for the binding of these receptors to viral-infected and tumor cells.

SUMMARY OF THE INVENTION

The present invention relates generally to peptide fragments derived from Natural Killer Cytotoxicity receptors (NCR) that are effective in targeting viral-infected cells and tumor cells in vivo. The present invention further relates to synthetic peptides and fusion proteins comprising these peptide sequences. It is now disclosed for the first time that peptides and fusion proteins, comprising active glycosylated fragments of the natural killer cytotoxicity receptors NKp44 and NKp46, were found to be effective in binding to viral-infected cells and tumor cells.

The present invention is based in part on the unexpected discovery that peptide fragments comprising glycosylation sites, derived from amino acid sequences of the human NKp46 receptor and of the human NKp44 receptor, retain the binding activity and the specificity to viral infected cells of the full-length receptors.

It is now disclosed that a single amino acid residue located within the proximal portion of the D2 domain of NKp46, is crucial for the recognition of both viral-infected cells and tumor cells by this natural cytotoxicity receptor. Within the D2 domain there is a short linker peptide designated NKp46LP (residues 215-254 of the full length protein; SEQ ID NO:3) joining this domain to the transmembrane segment of the receptor. Specifically, the present invention discloses that the Threonine residue at position 225 of the human NKp46 receptor is essential for the binding of NKp46 to viral-infected and tumor cells. Thus, Threonine 225 of NKp46, one of the O-glycosylated residues of this molecule, is an essential feature of an epitope involved in NK binding to target cells, and may be necessary for NK-mediated cell lysis.

It is further disclosed that a membrane linker peptide derived from the extracellular domain of the human NKp44 receptor comprising 55 amino acid residues is an essential feature in binding to viral infected cells. This linker peptide comprises a hyper-glycosylated region comprising at least 14 predicted glycosylation sites which contribute to the efficient binding to viral-infected cells. NKp44 receptor comprises the D domain, designated herein NKp44D (residues 22-135 of SEQ ID NO:5), and a tail or linker peptide designated herein NKp44LP (residues 136-190 of the mature full length receptor; SEQ ID NO:6).

In one aspect, the present invention provides isolated peptide sequences of NCRs that are necessary for recognition of target cells. It is to be clearly understood that the peptides of the invention are smaller than the intact domains of the NCRs from which they are derived. According to particular embodiments, the present invention provides fusion proteins and synthetic peptides comprising these isolated amino acid sequences of NCRs. It is further to be explicitly understood that the NCRs from which the active fragments are derived, may be of human or non-human origin. Though the human sequences are preferred, non-human primates or even lower mammalian species may be a suitable source for derivation of the active fragments according to the invention. It is further to be explicitly understood that the target cells may be human, as well as non-human mammalian or even avian, as it is known that relevant viral species may infect all of these genera.

According to one embodiment the present invention provides an essential epitope in the proximal domain of the human NKp46 receptor comprising the amino acid Threonine in position 225 (of the sequence of isoform a). According to some embodiments, the present invention provides fusion proteins and synthetic peptides comprising an amino acid sequence derived from the human NKp46 receptor as set forth in SEQ ID NO:3 comprising the amino acid Threonine in position 225, or an active fragment thereof. In a preferred embodiment, the Threonine amino acid residue at position 225 is covalently linked via various glycoforms to sialic acid. As disclosed herein, the sialylation of Threonine 225 is essential for the binding to viral-infected cells.

It will be appreciated by the skilled artisan that the glycosylation pattern of the relevant extracellular portion of a recombinant protein will be determined by the cell type in which it is produced. In order to optimize activity of the peptides or proteins of the invention the cell type for production by recombinant methods will be selected accordingly. It will further be appreciated that the peptides According to particular embodiments the active peptide fragment will be a sequence of 10-100 amino acids, according to certain preferred embodiments the active peptide fragment will be a sequence of about 20-80 amino acids, according to yet other embodiments the active peptide fragment will be a sequence of 30-60 amino acids. It will be noted that the unmodified linker peptide is composed of 40 amino acids, namely residues 215 to 254 in isoform a of the complete human 46 sequence of NKp46 (AJ001383). These 40aa are part of what we called NKp46D2 which includes both the Ig-like domain and the 40aa membrane linker peptide. Extensions or deletions of the linker peptide are explicitly encompassed in the present invention as long as they retain the biological activity of interest.

According to another embodiment, the present invention provides an isolated peptide from the extracellular domain of the human NKp44 receptor comprising the hyperglycosylated linker peptide, as set forth in SEQ ID NO:6 or any active fragment thereof.

According to one embodiment of the present invention, the present invention provides fusion proteins and synthetic peptides comprising a minimal epitope of NKp46. The minimal epitope of NKp46 will be an epitope that is capable of eliciting its action in targeting viral-infected cells via the hemagglutinin (HA) receptor. Furthermore, these peptides are capable of specific targeting of tumor cells. In one embodiment, the minimal epitope serves as a basis for the design of active fragments, derivatives and analogs of NKp46 comprising the minimal epitope which will possess similar or superior binding activity and stability as compared to the full-length NKp46 polypeptide.

According to other embodiments of the present invention provides a hyper-glycosylated fragment derived from the linker peptide of the intact NKp44 receptor located at the carboxy terminal of the proximal D extracellular domain. The present invention further provides fusion proteins and synthetic peptides comprising this linker peptide comprising a hyper-glycosylated fragment located in the NKp44 receptor. The present invention discloses that this linker peptide is an essential feature for the binding to viral-infected cells via the HA receptor.

The peptide derivatives of the present invention include peptides having at least one amino acid substitution, insertions, deletions, and conjugates so long as the peptides retain the binding activity and specificity of the respective NKp46 and NKp44 receptor domains.

In one embodiment, the peptide of the invention can serve as a basis for the design of active fragments of NKp46 and NKp44 receptors comprising the threonine residue 225 and the hyper-glycosylated sites, respectively, which will possess similar binding activity and stability as compared to the native NKp46 and NKp44 polypeptides.

The active fragments of NKp46 and NKp44 according to the present invention are not limited in size but are shorter than the intact domain. However, the invention particularly contemplates fragments having from about 10-100 amino acid residues in length, preferably from about 25-75 amino acid residues. It also contemplates proteins in which the core motif sequence, namely the amino acid sequences of the fragments of the present invention, is artificially implanted within a sequence of a polypeptide, such as peptides manufactured by recombinant DNA technology or chemical synthesis.

According to various embodiments, the active peptides of the present invention are conjugated to an immunoglobulin molecule or a fragment thereof, or to a cytotoxic substance which exhibit a cytotoxic effect on a target cell.

In another aspect, the present invention relates to a variant of NKp46 receptor polypeptide or an active fragment thereof having at least one amino acid substitution in an epitope required for the recognition of viral-infected cells or tumor cells. According to one embodiment, the NKp46 variant possesses higher binding affinity towards the target cells as compared to the wild type polypeptide. Thus, NK cells expressing this variant NKp46 may possess better toxic effect on the target cells. This NKp46 variant may be used in conditions in which activation of NK cells lysis is required, such as for example during viral infection or in malignant disorders. In a preferred embodiment, the key amino acid residue Threonine in position 225 of the NKp46 polypeptide is replaced with another residue, resulting in a polypeptide variant having higher binding affinity towards the target cells.

In another embodiment, the NKp46 variant, or an active fragment thereof possesses normal binding to the cellular target but does not activate the lysis process, thereby competing with the binding of NK cells to the target cells. This NKp46 variant may be used in conditions in which inhibition of NK cells lysis is required, for example, during organ transplantation or during gene therapy treatment involving the infection of the host cells with viral vectors. In a preferred embodiment, the key amino acid residue Threonine in position 225 of the NKp46 polypeptide is replaced with another residue, resulting in a variant having inhibitory effect on the binding of NK cells to the target cells.

In yet another embodiment, the NKp46 variant possesses diminished binding to the cellular target. In a preferred embodiment, the key amino acid residue Threonine in position 225 of the NKp46 polypeptide is replaced with another residue, preferably Alanine or Asparagine, resulting in a variant having diminished binding to the cellular target.

According to one embodiment, the amino acid substitution in the NKp46 variant modifies the binding of NKp46 to hemagglutinin (HA) of influenza virus in viral-infected cells. According to another embodiment, the amino acid substitution in the NKp46 variant modifies the binding of NKp46 to a specific cellular epitope expressed in tumor cells.

According to another aspect the present invention provides pharmaceutical compositions comprising an isolated peptide fragment of an NCR according to the invention. The pharmaceutical compositions may further comprise pharmaceutically acceptable diluents, carriers and excipients as are known in the art of drug formulation.

According to another aspect the present invention provides methods of treating a viral infection by administering to an individual in need thereof a composition comprising as an active ingredient a therapeutically effective amount of an isolated peptide fragment of an NCR according to the invention. According to one embodiment the pharmaceutical composition will comprise the hyperglycosylated fragment of NKp44. According to a further embodiment the viral infection will be a flu infection.

In another aspect, the present invention relates to a novel monoclonal antibody (mAb) which specifically recognizes an epitope in the membrane distal domain of NKp46. The binding of the monoclonal antibody of the present invention to the distal domain of NKp46 does not interfere with the binding of NKp46 to HA in viral-infected cells or with the selective binding of NKp46 to tumor cells. In a preferred embodiment, the present invention relates to a novel hybridoma named 461-G1, the mAb which is secreted by 461-G1 specifically recognizes an epitope in the distal fragment of NKp46 (NKp46D1). The binding of the mAb to NKp46 does not interfere with the binding of NKp46 to the target cell. Only background recognition was observed with the proximal fragment of NKp46 (NKp46-D2). In a preferred embodiment, the present invention thus relates to the isolated monoclonal antibody produced by hybridoma 461-G1.

The monoclonal antibodies of the present invention may be used inter alia for preparing bispecific antibodies capable of selective targeting of NK cells towards tumor cells and inducing tumor cell-specific lysis. The bispecific antibodies have the ability to maximize NK cytotoxicity against the growth of human tumors.

Thus, in one embodiment, an antibody specific for the distal domain of NKp46, as exemplified by the antibody secreted by the 461-G1 hybridoma, may be used for preparing bispecific antibodies. These bispecific antibodies may be used for selective targeting of NK cells towards tumor cells in order to induce tumor cell-specific lysis. In principle, the bispecific antibodies according to the present invention comprise two Fv regions of different classes, the first is directed against the D1 domain of NKp46 and the second is directed against a tumor-specific antigen, as well known in the art. The bispecific antibodies may be produced by fusing a hybridoma which secrets an antibody specific for the distal domain of NKp46, as exemplified by the 461-G1 hybridoma, with a second hybridoma which secrets monoclonal antibodies specific for a tumor-specific antigen. Following the fusion, a tetradoma (hybrid hybridoma) producing bispecific antibodies is formed.

Another aspect of the present invention relates to the use of an antibody specific for a domain of NKp46 receptor, as exemplified by the antibody secreted by the 461-G1 hybridoma, for selective removal of NK cells from a biological sample. Specifically, the present invention relates to a method for the selective removal of NK cells from a biological sample which comprises removal of those cells that are NKp46 positive. The method comprises contacting the biological sample with the isolated antibody of the invention or immunoreactive fragments thereof under condition appropriate for immune complex formation, and removing the immune complex formed from the biological sample.

According to various embodiments, a biological sample includes peripheral blood, plasma, bone marrow aspirates, lymphoid tissues, as well as cells isolated from cytapheresis, plasmapheresis and collection fluids such as synovial, cerebro-spinal, broncho-alveolar and peritoneal fluids.

The method for the selective removal of NK cells of the present invention may be used to treat individuals, particularly humans who would benefit from a decrease in NK cell activity. The method of this invention is particularly useful for treating those individuals whose NK cells have been activated. This invention is also particularly useful to treat individuals who are recipients or expecting to be recipients of transplant tissue e.g., bone marrow tissue, liver, kidney, heart and lung. Other individuals in need of treatment may include those suffering from an autoimmune disease. In addition, the method of this invention is useful for treating individuals in need of gene therapy involving infecting such an individual with a viral vector containing a therapeutic gene.

These and further embodiments will be apparent from the detailed description and examples that follow.

BRIEF DESCRIPTION OF THE DRAWINGS

FIG. 5 demonstrates that a specific mAb directed against the membrane distal domain (D1) of NKp46 do not block NK-mediated lysis of target cells. NK cells (FIG. 5a), BW (FIG. 5b) and BW transfected with NKp46 (FIG. 5c) were incubated with and without 461-G1 (thick black line) or control 12E7 (thin black line).

FIG. 9 Titration of NKp44-Ig, NKp44D-Ig and NKp44LP-Ig binding to tumor cells. PC-3 cells (FIG. 9a) or HeLa cells (FIG. 9b) were incubated with the indicated fusion proteins, followed by washing and incubation with FITC-conjugated goat antihuman Fc secondary antibody.

DETAILED DESCRIPTION OF THE INVENTION

Figure 1:
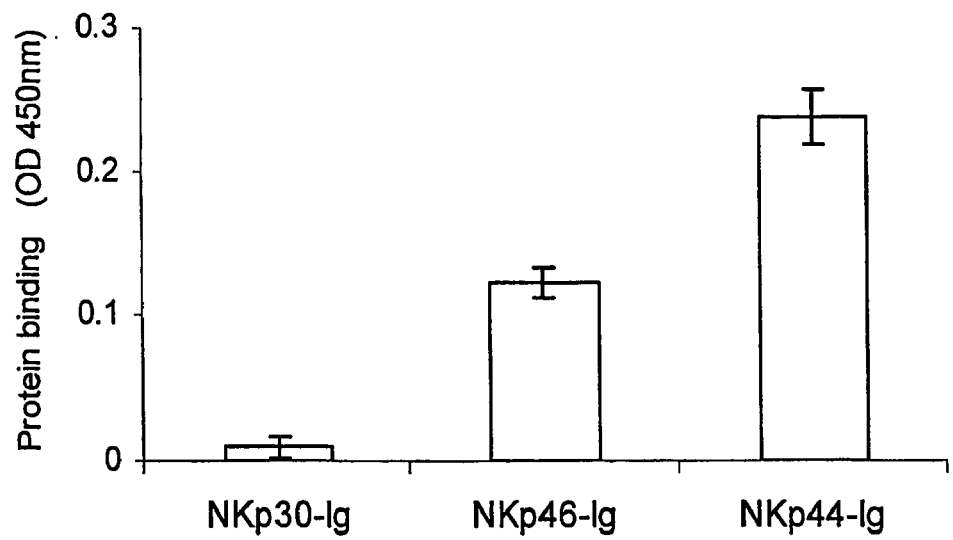
FIG. 1 demonstrates a direct binding of NKp46-Ig and NKp44-Ig to HA.
Figure 2A:
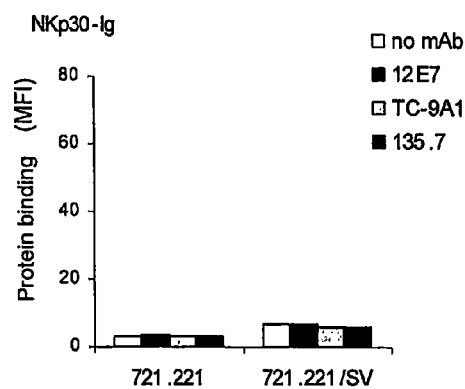
FIG. 2 demonstrates that the recognition of HA by NKp46 is mediated through the membrane proximal domain (NKp46D2). Uninfected and SV-infected 721.221 cells were incubated with or without monoclonal antibody (mAb) against HA (135.7) or control mAbs (12E7 and TC-9A1) and stained with the fusion proteins NKp30-Ig (FIG. 2a), NKp46-Ig (FIG. 2b), NKp46D2-Ig (FIG. 2c), or NKp46D1-Ig (FIG. 2d), followed by PE-conjugated goat antihuman antibodies.
Figure 2B:
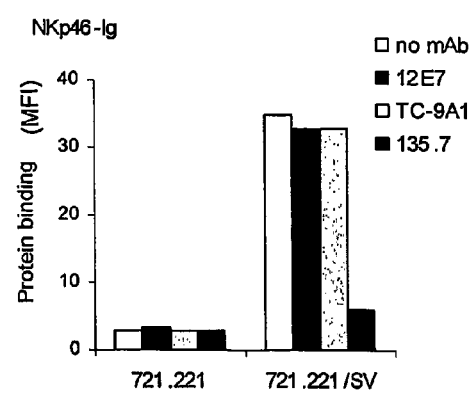
Figure 2C:
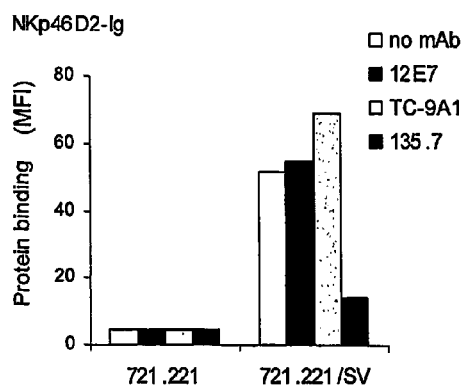
Figure 2D:
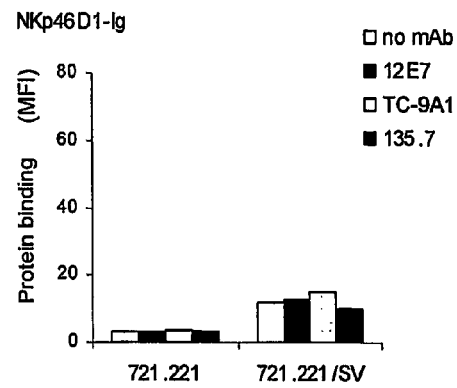

In order that this invention may be better understood, the following terms and definitions are herein provided.

The terms "NKp46" and "NKp44" refer to a natural cytotoxicity receptor expressed on NK cells preferably human which is capable of mediating direct killing of tumor and virus-infected cells.

The term "D1 fragment of NKp46" or "NKp46D1" refer to domain 1 (the distal domain) of the NKp46 molecule corresponding to amino acids 1-120 of NKp46 of isoform a.

The term "D2 fragment of NKp46" or "NKp46D2 refer to domain 2 (the proximal domain) of the NKp46 molecule corresponding to amino acids 121-254 of NKp46 of isoform a.

The term "NKp44LP" refers to the amino acid sequence for the truncated protein of NKp44, residues 109-169 (61 amino acid residues).

The term "NKp44D" refers to the amino acid sequence for the truncated protein of NKp44, residues 1-111.

The term "cytotoxic effect" refers to a killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell.

The term "bispecific antibodies" refers to monoclonal antibodies produced by hybrid hybridomas having two Fv regions directed against two different epitopes.

The term "specific binding" as used herein refers to the preferential association of a molecule with a cell or tissue bearing a particular target molecule or marker and not to cells or tissues lacking that target molecule or expressing that target molecule at low levels. It is, of course, recognized that a certain degree of non-specific interaction may occur between a molecule and a non-target cell or tissue.

The term "conjugate" refers to a polypeptide formed by the joining of two or more polypeptides through a peptide bond formed between the amino terminus of one polypeptide and the carboxyl terminus of another polypeptide. The conjugate may be formed by the chemical coupling of the constituent polypeptides or it may be expressed as a single polypeptide fusion protein from a nucleic acid sequence encoding the single contiguous conjugate. In those instances where the active segment of the conjugate is a cytotoxic agent that is not a polypeptide it is to be understood that the cytotoxic agent is attached via chemical coupling to the polypeptide.

The term "active fragments" refers to "fragments", "variants", "analogs" or "derivatives" of the molecule. A "fragment" of a molecule, such as any of the nucleic acid or the amino acid sequence of the present invention is meant to refer to any nucleotide or amino acid subset of the molecule. A "variant" of such molecule is meant to refer to a naturally occurring molecule substantially similar to either the entire molecule or a fragment thereof. An "analog" of a molecule is a homologous molecule from the same species or from different species. The amino acid sequence of an analog or derivative may differ from the specific molecule, e.g. the NKp46 or NKp44 receptors, used in the present invention when at least one residue is deleted, inserted or substituted.

The term "cellular ligand" refers generally to tumor cell membrane molecules capable of reacting with the target recognition segment of the conjugate of the invention.

The term "target cells" refers to cells that are killed by the cytotoxic activity of the peptide of the invention. The target cells express the ligand for at least one of NKp46, molecule and include, in particular, cells that are infected by a virus, cells that are malignant or otherwise derived from solid as well as non-solid tumors. The target cell is of mammalian origin selected from the group consisting of human cells, primate cells and mouse cells.

The term "cell-mediated cytotoxicity or destruction" refers to antibody-dependent, cell-mediated cytotoxicity (ADCC) and natural killer (NK) cell killing.

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein the term "peptide fragment" includes native peptides (either degradation products, artificially synthesized peptides or recombinant peptides) and peptido-mimetics (typically artificially synthesized peptides). As used herein the terms "peptide fragment" refers preferably to molecules of 10 to 100 amino acids, with molecules of 20 to 80 amino acids and those of 30 to 60 amino acids more preferred. Exemplary peptides may be generated by any of the methods known in the art, including conservative or non-conservative replacements of known sequences, or derived by digestion of proteins.

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

"Transient transfection" refers to cases where exogenous DNA does not integrate into the genome of a transfected cell, e.g., where episomal DNA is transcribed into mRNA and translated into protein.

As used herein, the term "vector" refers to a nucleic acid molecule capable of transporting another nucleic acid to that it has been linked. One type of vector is a genomic integrated vector, or "integrated vector", which can become integrated into the chromsomal DNA of the host cell. Another type of vector is an episomal vector, i.e., a nucleic acid capable of extra-chromosomal replication. Vectors capable of directing the expression of genes to that they are operatively linked are referred to herein as "expression vectors". In the present specification, "plasmid" and "vector" are used interchangeably unless otherwise clear from the context.

The present invention is based on the first direct proof that a specific epitope in the proximal domain of NKp46 receptor is necessary for the binding of NKp46 to viral-infected and tumor cells. NKp46 displays two putative O-linked glycosylation sites at Threonine 125 and Threonine 225, and one N-linked glycosylation site at Asparagine 216. All three putative sites are located within the D2 domain of NKp46 receptor. The inventors of the present invention now disclose that substitution of Thr125 or Asn216 with Alanine (NKp46T125A and NKp46N216A, respectively) had no significant effect on the binding to the infected cells (see example 5). However, substitution of Thr225 with Alanine resulted in a sharp decrease in the enhanced binding to the infected cells. It should be understood that substitution of Thr225 with Serine which is an alternative residue for potential O-glycosylation, and thus shares greater resemblance to threonine, resulted in a decrease in binding to viral-infected cells, but showed similar binding to tumor cells.

Specifically, the inventors of the present invention have unexpectedly discovered that the recognition of both viral-infected cells as well as tumor cells by NKp46 is dependent on the amino acid Threonine located in position 225 of NKp46. Importantly, while sialylation of Threonine 225 is essential for the recognition and lysis of viral-infected cells, the role of Threonine 225 in tumor cell recognition does not involve its sialylation. Thus, the amino acid Threonine at position 225 of NKp46 seems to play a dramatic role in the recognition of various targets by NK cells via different mechanisms. Indeed, this amino acid is preserved in NKp46 of human, murine and primates with the exception of cattle that express Valine in this position. This evolutionary preservation may also explain the fact that human NKp46 recognizes murine tumor lines with considerable efficiency[5-7,9].

In addition, the present invention relates to NKp44 linker peptide (NKp44LP). NKp44 is expressed specifically on activated NK cells and NKp44 can also recognize the HA protein of both Influenza virus (IV) and Sendai virus (SV) in a similar way to that of NKp46[14] The binding of NKp44 to HA improves the ability of some NK clones to lyse virus-infected cells and can overcome the inhibition mediated by MHC-class I proteins. NKp44 has only one extracellular domain (residues 1-114, Ig-like V domain) and rather long membrane linker peptide (55 amino acids long, residues 115-169)[7]. It was demonstrated that glycosylation, and specifically the sialylation of the NKp44 receptor is required for the binding to viral HA from Influenza virus in a similar manner to that observed for the NKp46 receptor. Thus, out of four receptors involved in lysis (CD16, NKp30, NKp44 and NKp46) identified on the surface of human NK cells, two (NKp44 and NKp46) bind HA, whereas the other two (CD16 and NKp30) did not[14].

Additional viruses families that express hemagglutinins and may be amenable to treatment with the compositions and methods of the present invention are Adenoviridae, Poxyiridae, Picornaviridae, Flaviviridae, Orthomyxoviridae, Paramyxoviridae, Coronaviridae.

Synthesis of Peptides of the Invention

The peptides of the invention can be produced by any known method of producing an amino-acid sequence, such as, controlled degradation of a purified protein by proteases or other chemical methods (Allen G., Sequencing of proteins and peptides, 1989, Elsevier Science Publishers B.V.). Chemical synthesis is commonly performed by coupling of the amino acid residues or peptide fragments to one another in correct order in liquid phase to produce the desired peptide. Another common strategy is the coupling of the amino acids to one another starting with a solid phase (resin) to which the C-terminal of the last amino acid of the sequence is coupled, whereupon the C-terminal of the penultimate amino acid is coupled to the N-terminal of the last amino acid, etc., finally releasing the built-up peptide from the solid phase (so called solid-phase technique).

Peptide fragments could also be produced by methods well known to one skilled in the art of biotechnology. For example, using a nucleic acid selected from the group including DNA, RNA, or cDNA. The desired fragments may be produced in live cell cultures and may be purified after cell harvesting as known in the art.

According to one embodiment, it is possible to characterize and isolate a minimal epitope of NKp46. The minimal epitope of NKp46 will be an epitope that is still capable of eliciting its action in targeting viral-infected cells via the hemagglutinin (HA) receptor. Furthermore, the minimal epitope is still capable of specific targeting of tumor cells. In one embodiment, the minimal epitope can serve as a basis for the design of active fragments of NKp46 comprising the minimal epitope which will possess similar or superior binding activity and stability as compared to the full-length NKp46 polypeptide.

In order to characterize a minimal epitope of NKp46 for targeting viral-infected cells or tumor cells, the NKp46 sequence can be shortened by deleting amino acid residues from each end of the polypeptide until the smallest effective NKp46 derivative which comprises amino acid Threonine 225 is obtained. Lysis of melanoma cells is a very convenient assay system to detect the ability of the peptide derivatives to activate the lysis response. Such assays are detailed in the Examples below.

Once the minimal effective epitope of NKp46 is identified, it is possible to substitute each position with another amino acid residue and uncover the key residues required for binding to viral-infected cells or tumor cells. These key residues can then be substituted to discover more effective variant peptides. Likewise, the same amino acid substitution procedure can be used to discover inhibitor peptides: blocking peptides that bind, but do not activate the lysis process.

Once the minimal and optimal peptide is characterized, it would be also possible to synthesize non-peptidic analogues that would have the structure of the active epitope, but which would be resistant to enzymatic degradation. Such analogues would have extended half-lives and be more effective in their lysis activity.

The present invention encompasses any analog, derivative, and conjugate containing the peptides of the invention, the amino acid sequence of which is shown herein so long as the peptide is capable of binding to hemagglutinin (HA) receptor on viral-infected cells or to tumor cells. Thus, the present invention encompasses peptides containing non-natural amino acid derivatives or non-protein side chains.

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

A peptide derivative refers to a peptide having an amino acid sequence that comprises the amino acid sequence of the peptide of the invention. Thus, the peptides of the present invention can be subject to various changes, substitutions, insertions, and deletions where such changes do not destroy the biological activity of the peptide. In this regard, a peptide of this invention corresponds to amino acid sequence of NKp46D2, where one or more changes are made so long as the peptide retains the desirable function of peptide of the invention in one or more of the assays as defined herein.

The term "derivative" includes any chemical derivative of the peptide of the invention having one or more residues chemically derivatized by reaction of side chains or functional groups. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxyl-amidation, e.g., with ammonia, methylamine, and the like.

Peptides of the present invention also include any peptide having one or more additions and/or deletions of residues relative to the sequence of the peptide of the invention, the sequence of which is shown herein, so long as the requisite inhibitory activity is maintained.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

A peptide of the invention may also be conjugated to itself or aggregated in such a way as to produce a large complex containing the peptide. Such large complex may be advantageous because it has new biological properties such as longer half-life in circulation or greater activity.

The present invention relates to a pharmaceutical composition comprising as an active ingredient a conjugate comprising a target recognition segment comprising an NCR or an active fragment thereof, the NCR selected from the group consisting of: NKp46 and NKp44, or a functional fragment thereof that binds to a cellular ligand expressed on the surface of a target tumor cell or viral-infected cell; and an active segment comprising an active agent that promotes the lysis of the target cell; and a pharmaceutically acceptable carrier, stabilizer or diluent.

The composition of the invention comprises a pharmaceutically acceptable diluent or carrier. The compositions according to the invention will in practice normally be administered orally or by injection. As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated. The dosage administered will be dependent upon the age, sex, health condition and weight of the recipient, and the nature of the effect desired.

The pharmaceutical compositions of this invention are particularly useful for parenteral administration, such as intravenous administration or administration into a body cavity or lumen of an organ. The compositions for administration will commonly comprise a solution of the conjugate molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the conjugate in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as Remington's Pharmaceutical Science, 18th ed., Mack Publishing.

For oral administration tablets and capsules may contain conventional excipients, such as binders, for example syrup, sorbitol, or polyvinyl pyrrolidone; fillers, for example lactose, microcrystalline cellulose, corn starch, calcium phosphate or sorbitol; lubricants, for example magnesium stearate, stearic acid, polyethylene glycol or silica; disintegrates, for example potato starch or sodium starch glycolate, or surfactants, such as sodium lauryl sulphate.

Oral liquid preparations can be in the form of for example water or oil suspensions, solutions, emulsions, syrups or elixirs, or can be supplied as a dry product for constitution with water or another suitable vehicle before use.

It is proposed that the various methods and compositions of the invention will be broadly applicable to the treatment of any tumor, including solid and non-solid tumors. If the tissue is a part of the lymphatic or immune systems, malignant cells may include non-solid tumors of circulating cells. Malignancies of other tissues or organs may produce solid tumors. Exemplary solid tumors to which the present invention is directed include but are not limited to carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like. Exemplary non-solid tumors to which the present invention is directed include but are not limited to B cell Lymphoma, T cell Lymphoma, or Leukemia such as Chronic Myelogenous Leukemia.

The Sequence ID Numbers of the full length receptors which appear in the application are:

```
SEQ ID NO:1 NKp46 (O76036) protein isoform a
  1 MSSTLPALLC VGLCLSQRIS AQQQTLPKPF IWAEPHFMVP
    KEKQVTTCCQ GNYGAVEYQL

61 HFEGSLFAVD RPKPPERINK VKFYIPDMNS RMAGQYSCIY
    RVGELWSEPS NLLDLVVTEM
```

-continued

```
121 YDTPTLBVHP GPEVISGEKV TFYCRLDTAT SMFLLLKEGR
    SSHVQRGYGK VQAEFPLGPV

181 TTAHRGTYRC FGSYNNHAWS FPSEPVKLLV TGDIENTSLA
    PEDPTFPADT WGTYLLTTET

241 GLQKDHALWD HTAQNLLRMG LAFLVLVALV WFLVEDWLSR
    KRTRERASRA STWEGRRRLN

301 TQTL
```

Unmarked letters leader sequence residues 1-21
Italic letter NKp46D1 residues 22-120
Bold letters NKp46D2 residues 121-254
Underlined letter is Threonine 225

```
SEQ ID NO: 4 NKp44 (CAC09453) protein
  1 MAWRALHPLL LLLLLFPGSQ AQSKAQVLQS VAGQTLTVRC
    QYPPTGSLYE KKGWCKEASA

61 LVCIRLVTSS KPRTMAWTSR FTIWDDPDAG FFTVTMTDLR
    EEDSGHYWCR IYRPSDNSVS

121 KSVRFYLVVS PASASTQTSW TPRDLVSSQT QTQSCVPPTA
    GARQAPESPS TIPVPSQPQN

181 STLRPGPAAP IALVPVFCGL LVAKSLVLSA LLVWWVLRNR
    HMQHQGRSLL HPAQPRPQAH

241 RHFPLSHRAP GGTYGGKP
```

Unmarked letters leader sequence residues 1-21
Italic letters NKp44D residues 22-135
Bold letters NKp44LP residues 136-190

PCT/IL03/01040 relates to conjugates and fusion proteins of Natural Killer cytotoxic receptors NKp30, NKp46 and NKp44, or active fragments thereof and an active agent selected from a cytotoxic drug or an Ig fragment effective in targeting tumor cells in vivo.

It is to be explicitly understood the present invention exclude any one of SEQ ID NO:13-18, as listed below:

```
SEQ ID NO:13 NKp46-Fc conjugate
MSSTLPALLCVGLCLSQRISAQQQTLPKPFIWAEPHFMVPKEKQVTICCQ

GNYGAVEYQLHFEGSLFAVDRPKPPERINKVKFYIPDMNSRMAGQYSCIY

RVGELWSEPSNLLDLVVTEMYDTPTLSVHPGPEVISGEKVTFYCRLDTAT

SMFLLLKEGRSSHVQRGYGKVQAEFPLGPVTTAHRGTYRCFGSYNNHAWS

FPSEPVKLLVTGDIENTSLAPEDPTFPADTWGTYLLTTETGLQKDHALWD

HTAQDPEPKSSDKTHTCPPCPAPEFEGAPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSK

LTVDKSRWQQGNVFSCSVMHEALHNHYTQKSLSLSPGK
```

Unmarked letters designate origin leader peptide
Underlined letters designate D1 region
Bold letters designate D2 region
Italic letters designate Fc region (234 amino acid)

```
SEQ ID NO:14 NKp46D1-Fc conjugate
MGMPMGSLQPLATLYLLGMLVASCLGRLRVPQQQTLPKPFIWAEPHFMVP
```

-continued
KEKQVTICCQGNYGAVEYQLHFEGSLFAVDRPKPPERINKVKEYIPDMNS

RMAGQYSCIYRVGELWSEPSNLLDLVVTEM*DPEPKSSDKTHTCPPCPAPE*

*FEGAPSVFLFPPKPKDTLMISRTPEVTCVVVDVSHEDPEVKFNWYVDGVE*

*VHNAKTKPREEQYNSTYRVVSVLTVLHQDWLNGKEYKCKVSNKALPAPIE*

*KTISKAKGQPREPQVYTLPPSRDELTKNQVSLTCLVKGFYPSDIAVEWES*

*NGQPENNYKTTPPVLDSDGSFFLYSKLTVDKSRWQQGNVFSCSVMHEALH*

*NHYTQKSLSLSPGK*

Unmarked letters designate leader peptide of CD5
Underlined letters designate KpnI site (5 amino acid)
Bold letters designate D2 region (128 amino acid)
Italic letters designate Fc region (234 amino acid)

```
SEQ ID NO: 15 NKp46D2-Fc conjugate
MGMPMGSLQPLATLYLLGMLVASCLGRLRVPYDTPTLSVHPGPEV
```

ISGEKVTFYCRLDTATSMFLLLKEG RSSHVQRGYGKVQAEFPLG

PVTTAHRGTYRCFGSYNNHAWSFPSEPVKLLVTGDIENTSLAPED

PTFPDTWGTYLLTTETGLQKDHALW*DPEPKSSDKTHTCPPCPAPE*

*FEGAPSVFLFPPKPKDTLMISRTPEVTCVVVDVSHEDPEVKFNWY*

*VDGVEVHNAKTKPREEQYNSTYRVVSVLTVLHQDWLNGKEYKCKV*

*SNKALPAPIEKTISKAKGQPREPQVYTLPPSRDELTKNQVSLTCL*

*VKGFYPSDIAVEWESNGQPENNYKTTPPVLDSDGSFFLYSKLTVD*

*KSRWQQGNVFSCSVMHEALHNHYTQKSLSLSPGK*

Unmarked letters designate leader peptide of CD5
Underlined letters designate KpnI site (5 amino acid)
Bold letters designate NKp44 region
Italic letters designate Fc region (234 aminoacid)

```
SEQ ID NO:16 NKp44-Fc conjugate
MGMPMGSLQPLATLYLLGMLVASCLGRLRVPQSKAQVLQSVAGQTLTVRC
```

QYPPTGSLYEKKGWCKEASALVCIRLVTSSKPRTVAWTSRFTIWDDPAG

FFTVTMTDLREEDSGHYWCRIYRPSDNSVSKSVRFYLVVSPASASTQTSW

TPRDLVSSQTQTQSCVPPTAGARQAPESPSTIPVPSQPQNSTLRPGPAAP

*DPEPKSSDKTHTCPPCPAPEFEGAPSVFLFPPKPKDTLMISRTPEVTCVV*

*VDVSHEDPEVKFNWYVDGVEVHNAKTKPREEQYNSTYRVVSVLTVLHQDW*

*LNGKEYKCKVSNKALPAPIEKTISKAKGQPREPQVYTLPPSRDELTKNQV*

*SLTCLVKGFYPSDIAVEWESNGQPENNYKTTPPVLDSDGSFFLYSKLTVD*

*KSRWQQGNVFSCSVMHEALHNHYTQKSLSLSPGK*

Unmarked letters designate leader peptide of CD5
Underlined letters designate KpnI site (5 amino acid)
Bold letters designate NKp44-DS region
Italic letters designate Fc region (234 amino acid)

```
SEQ ID NO:17 NKp44DS-Fc conjugate
MGMPMGSLQPLATLYLLGMLVASCLGRLRVPSPASASTQTSWTPRDLVSS
```

QTQTQSCVPPTAGARQAPESPSTIPVPSQPQNSTLRPGPAAP*DPEPKSSD*

*KTHTCPPCPAPEFEGAPSVFLFPPKPKDTLMISRTPEVTCVVVDVSHEDP*

*EVKFNWYVDGVEVHNAKTKPREEQYNSTYRVVSVLTVLHQDWLNGKEYKC*

*KVSNKALPAPIEKTISKAKGQPREPQVYTLPPSRDELTKNQVSLTCLVKG*

*FYPSDIAVEWESNGQPENNYKTTPPVLDSDGSFFLYSKLTVDKSRWQQGN*

*VFSCSVMHEALHNHYTQKSLSLSPGK*

Unmarked letters designate leader peptide of CD5
Underlined letters designate KpnI site (5 amino acid)
Bold letters designate NKp44-DL region
Italic letters designate Fc region (234 amino acid)

```
SEQ ID NO:18 NKp44DL-Fc conjugate
MGMPMGSFQPLATLYLLGMLVASCLGRLRVPQSKAQVLQSVAGQTLTVRC
```

QYPPTGSLYEKKGWCKEASALVCIRLVTSSKPRTVAWTSRFTIWDDPAG

FFTVTMTDLREEDSGHYWCRIYRPSDNSVSKSVRFYLVVSPA*DPEPKSSD*

*KTHTCPPCPAPEFEGAPSVFLFPPKPKDTLMISRTPEVTCVVVDVSHEDP*

*EVKFNWYVDGVEVHNAKTKPREEQYNSTYRVVSVLTVLHQDWLNGKEYKC*

*KVSNKALPAPIEKTISKAKGQPREPQVYTLPPSRDELTKNQVSLTCLVKG*

*FYPSDIAVEWESNGQPENNYKTTPPVLDSDGSFELYSKLTVDKSRWQQGN*

*VFSCSVMHEALHNHYTQKSLSLSPGK*

Unmarked letters designate leader peptide of CD5
Underlined letters designate KpnI site(5 amino acid)
Bold letters designate NKp44-DL region
Italic letters designate Fc region (234 amino acid)

```
SEQ ID NO:19 NKp46 isoform b (Accession No.
CAA06872)
MSSTLPALLCVGLCLSQRISAQQQTLPKPFIWAEPHFMVPKEKQVTICCQ
GNYGAVEYQLHFEGSLFAVDRPKPPERINKVKFYIPDMNSRMAGQYSCIY
RVGELWSEPSNLLDLVVTEMYDTPTLSVHPGPEVISGEKVTFYCRLDTAT
SMFLLLKEGRSSHVQRGYGKVQAEFPLGPVTTAHRGTYRCFGSYNNHAWS
FPSEPVKLLVTGDIENTSLAPEDPTFPDHALWDHTAQNLLRMGLAFLVLV
ALVWFLVEDWLSRKRTRERASRASTWEGRRRLNTQTL SEQ ID NO:20 NKp46 isoform c (Accession No.
CAA06873)
MSSTLPALLCVGLCLSQRISAQQQMYDTPTLSVHPGPEVISGEKVTFYCR
LDTATSMFLLLKEGRSSHVQRGYGKVQAEFPLGPVTTAHRGTYRCFGSYN
NHAWSFPSEPVKLLVTGDIENTSLAPEDPTFPADTWGTYLLTTETGLQKD
HALWDHTAQNLLRMGLAFLVLVALVWFLVEDWLSRKRTRERASRASTWEG
RRRLNTQTL SEQ ID NO:21 NKp46 isoform d (Accession No.
CAA06874)
MSSTLPALLCVGLCLSQRISAQQQMYDTPTLSVHPGPEVISGEKVTFYCR
LDTATSMFLLLKEGRSSHVQRGYGKVQAEFPLGPVTTAHRGTYRCFGSYN
NHAWSFPSEPVKLLVTGDIENTSLAPEDPTFPDHALWDHTAQNLLRMGLA
FLVLVALVWFLVEDWLSRKRTRERASRASTWEGRRRLNTQTL
```

Monoclonal Antibody—Preparation and Use Thereof

In another aspect, the present invention relates to a novel monoclonal antibody (mAb) which specifically recognizes an epitope in the membrane distal domain of NKp46. The binding of the monoclonal antibody of the present invention to the distal domain of NKp46 does not interfere with the binding of NKp46 to HA in viral-infected cells or with the specific NKp46 binding site on tumor cells. In the case of a monoclonal antibody, antibody-producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced.

In one embodiment, the present invention relates to a novel hybridoma named 461-G1, the mAbs which is secreted by the 461-G1 hybridoma specifically recognizes the distal fragment of NKp46 (NKp46D1) and the NKp46D1-Ig fusion protein whereas only background recognition was observed with the proximal domain (NKp46-D2).

In one embodiment, the present invention thus relates to the isolated monoclonal antibody produced by hybridoma 461-G1 as described in the Examples below. The isolated antibody of the invention can be coupled to any appropriate label for visualization purposes. Such labels include e.g. the fluorescent labels, the radioactive labels, the enzymatic labels.

The monoclonal antibodies of the invention can be prepared using any technique that provides for the production of antibody molecules by cell lines in culture. These include, but are not limited to, the original techniques of Köhler and Milstein, Nature, 265:495-497 (1975), modified as described in Anderson et al., J. Immunol., 143:1899 (1989).

The antibody may be administered to the patient by any immunologically suitable route, such as intravenous, intraperitoneal, subcutaneous, intramuscular or intralymphatic routes, however the intravenous route is preferred. The clinician may compare the anti-idiotypic and anti-isotypic responses associated with these different routes in determining the most effective route of administration. After this treatment, the reduced antibody may be frozen or lyophilized for storage purposes.

Screening procedures that can be used to screen hybridoma cells producing antibodies to NKp46 includes, but are not limited to (1) enzyme-linked immunoadsorbent assays (ELISA), (2) immunoprecipitation or (3) fluorescent activated cell sorting (FACS) analyses. Many different types of ELISA that can be used to screen for anti-NKp46 monoclonal antibodies can be envisioned by persons skilled in the art.

Initial screening is preferably conducted by screening hybridoma supernatants by flow cytometry for their reactivity with NK cells, but not with T cells, and monocytes. Further characterization of the hybridoma can be conducted by testing of purified populations of lymphoid and non-lymphoid cells by indirect immunofluorescence assays and flow cytometry. Monoclonal antibodies that recognize NKp46 epitopes will react with an epitope that is present on a high percentage NK cells e.g., at least about 70-90%, e.g. about 80%, of such cells, but will not significantly react with CD3+ T cells or CD20+B cells. In preferred embodiments, the antibody will not react with monocytes, granulocytes, platelets, and red blood cells.

Once the desired hybridoma has been selected and cloned, the resultant antibody may be produced in one of two major ways. The purest monoclonal antibody is produced by in vitro culturing of the desired hybridoma in a suitable medium for a suitable length of time, followed by the recovery of the desired antibody from the supernatant. The length of time and medium are known or can readily be determined. This in vitro technique produces essentially monospecific monoclonal antibody, essentially free from other species of anti-human immunoglobulin. However, the in vitro method may not produce a sufficient quantity or concentration of antibody for some purposes, since the quantity of antibody generated is only about 50 μg/ml.

To produce a much larger quantity of monoclonal antibody, the desired hybridoma may be injected into an animal, such as a mouse. Preferably the mice are syngeneic or semi-syngeneic to the strain from which the monoclonal-antibody producing hybridomas were obtained. Injection of the hybridoma causes formation of antibody producing tumors after a suitable incubation time, which will result in a high concentration of the desired antibody (about 5-20 mg/ml) in the ascites of the host animal.

Antibody molecules can be purified by known techniques e.g. by immunoabsorption or immunoaffinity chromatography, chromatographic methods such as high performance liquid chromatography or a combination thereof.

Following these protocols, any person skilled in this area of technology can readily isolate hybridomas that produce a monoclonal antibody of the invention, and in particular a monoclonal antibody exhibiting specificity for the distal domain of NKp46. Examples of such hybridomas are described in the Examples below.

In another aspect, the invention relates to isolated immunoreactive fragments of the antibody of the invention. Such fragments notably include Fab, F(ab')$_2$, and CDR antibody fragments. The skilled person will note that humanized antibodies of the invention can be derived therefrom as desired, notably when intended to be administered to a human person. By "immuno-reactive fragments of an antibody", it is meant any antibody fragment comprising the antigen binding-site.

Such fragments thus include F(ab')$_2$ fragments obtained either by enzymatic digestion of said antibody by proteolytic enzymes such as pepsin or Papain, and Fab fragments derived thereof by reduction of the sulfhydryl groups located in the hinge regions, as known by any skilled person. Immunoreactive fragments can also comprise recombinant single chain or dimeric polypeptides whose sequence comprises the CDR regions of the antibody of interest. Isolated CDR regions themselves are also contemplated within the definition of the isolated immuno-reactive fragments of the invention.

In another aspect, a hybridoma which secrets antibodies directed against the distal domain of NKp46, such as for example the 461-G1 hybridoma, may be used for preparing bispecific antibodies capable of selective targeting of NK cells towards tumor cells and induction of tumor cell-specific lysis. The bispecific antibodies have the ability to induce a maximum NK cytotoxicity whereby the growth of human tumors will not be just impeded, but instead a complete remission of established human tumors may be achieved.

In principle, the bispecific antibodies according to the present invention comprise two Fv regions of different classes, the first is directed against the D1 domain of NKp46 and the second is directed against a tumor-specific antigen. In a preferred embodiment, the bispecific antibodies may be produced by fusing the 461-G1 hybridoma of the present invention with a second hybridoma which secrets monoclonal antibodies specific for a tumor-specific antigen. Following the fusion, a tetradoma (hybrid hybridoma) producing bispecific antibodies is formed.

As is well known, Fv, the minimum antibody fragment which contains a complete antigen recognition and binding site, consists of a dimer of one heavy and one light chain variable domain ($V_H$ and $V_L$) in non-covalent association. In this configuration that corresponds to the one found in native antibodies the three complementarity determining regions (CDRs) of each variable domain interact to define an antigen binding site on the surface of the $V_H$-$V_L$ dimer. Collectively, the six CDRs confer antigen binding specificity to the antibody. Frameworks (FRs) flanking the CDRs have a tertiary structure that is essentially conserved in native immunoglobulins of species as diverse as human and mouse. These FRs serve to hold the CDRs in their appropriate orientation. The constant domains are not required for binding function, but may aid in stabilizing $V_H$-$V_L$ interaction. Even a single variable domain (or half of an Fv comprising only three CDRs specific for an antigen) has the ability to recognize and bind antigen, although usually at a lower affinity than an entire binding site.

The preparation of bispecific antibodies obtained by hybrid hybridoma technology (tetradoma technology) is disclosed for example in U.S. Pat. No. 5,643,759. These tetradomas produce bispecific antibodies, which link the NK cells via the NKp46 receptor with tumor cells via specific tumor-associated antigens.

U.S. Pat. No. 6,723,538 discloses bispecific antibodies comprising a chemokine receptor binding domain and a T cell surface polypeptide or cell toxin binding domain and methods for preparing bispecific antibodies. U.S. Pat. No. 6,719,971 discloses methods for preparing humanized antibodies and bispecific antibodies. U.S. Pat. No. 6,703,018 discloses methods for generating bispecific humanized CD11a antibodies having binding specificities for at least two different epitopes.

The hybridoma cells and the tetradoma cells can be prepared in the following manner: Immunized BALB/C mouse spleen cells are fused with mouse myeloma cells in a known manner. The hybridoma cells which have the highest affinity to NKp46 are selected. This line is propagated in a known manner by injection into BALB/c mice and obtained from the ascites by chromatographic purification. To prepare the tetradoma cells with two light chains of different classes (lambda and kappa), the 461-G1 hybridoma cells are fused with hybridoma cells producing monoclonal antibodies directed against tumor-specific antigens. Examples of monoclonal antibodies directed against tumor-specific antigens are disclosed for example in U.S. Pat. Nos. 5,204,095; 5,196,337; 5,134,075, 5,171,665; 6,342,221, 5,965,132, 6,004,554, 6,071,491, 6,017,514, 5,882,626 and 5,019,368.

After testing for bispecific reactivity, for example by the detection of antibodies with different light-chain content by indirect immunofluorescence, the mixed tetradoma cell clone is obtained which has the strongest possible simultaneous expression of the two light chains, and then purified by chromatography.

The bispecific antibodies of the invention can be formulated by known methods, e.g., as a solution of the lyophilized protein, and serves for parenteral application in humans, while adjuvants and additives known to the expert can be present.

Alternative methods known in the art for constructing bispecific antibodies are by covalently linking specific antibodies or by other approaches, like the diabody approach.

The present invention also relates to a method for the selective removal of NK cells from a biological sample which comprises the selective removal of those cells that are NKp46 positive. Such a method comprises contacting the biological sample with the isolated antibody of the present invention or the immunoreactive fragments thereof under condition appropriate for immune complex formation, and removing the immune complex thus formed.

According to various embodiments, a biological sample includes peripheral blood, plasma, bone marrow aspirates, lymphoid tissues, as well as cells isolated from cytapheresis, plasmapheresis and collection fluids such as synovial, cerebro-spinal, broncho-alveolar and peritoneal fluids.

The method for the selective removal of NK cells of the present invention may be used to treat mammals, particularly humans who would benefit from a decrease in NK cell activity. The method of this invention is particularly useful for treating those individuals whose NK cells have been activated. This invention is also particularly useful to treat individuals who are recipients or expecting to be recipients of transplant tissue e.g., bone marrow tissue, liver, kidney, heart and lung. Other individuals in need of treatment may include those suffering from an autoimmune disease. In addition, the method of this invention is useful for treating individuals in need of gene therapy involving infecting such an individual with a viral vector containing a therapeutic gene.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Experimental Methods:
Cells and Viruses
The following cell lines were used: melanoma cell lines (1106mel, LBmelA1, 1259mel, 1076mel), prostate carcinoma cell lines PC3, human prostate adenocarcinoma derived from bone metastasis that is PSA negative and Androgen insensitive (ATCC no. CRL-1435), and LN-CAP). EBV transformed B cells (DAUDI, 721.221) and the mouse P815 line. HeLa is a human cervical adenocarcinoma (ATCC no. CCL-2).

The generation of BW cells expressing NKp46 was previously described[13].

The SV was purchased from Spafas (Preston City, Conn.). The influenza A/Beijing (A/Beijing/262/95-like (H1N1)), A/Sydney (A/Sydney/5/97-like (H3N2)), and A/Moscow (A/Moscow/10/99-like (H3N2)) viruses were propagated by injecting 0.2 ml of stock virus diluted 1/1000 into the allantoic sac of 11-day-old embryonated chicken eggs. After incubation for 48 hrs at 37° C. and 16 hrs at 4° C., ~8 ml of virus-rich allantoic fluid was removed and checked for viral presence by hemagglutination with chicken erythrocytes (0.5% w/w, 0.1 ml–A/Sydney=512 HA units, A/Moscow=32 HA units, A/Beijing=32 HA units). The viruses were then stored at −70° C. until use. The cells were infected by incubating one million cells overnight in 3 ml complete medium (RPMI 1640+10% FCS) at 37° C. and 5% $CO_2$ with 100 μl of different virus strains.

Monoclonal Antibodies and Anti-Virus Sera
The anti CD99 mAb 12E7 is a kind gift from a. Bernard (Hospital de L'Archet, Nice, France). The generation of the 135.7 mAb directed against SV-HA was previously described[13]. Human sera were obtained from individuals immunized 1 month earlier with the trivalent influenza vaccine and having high titers (500-2500 HI titer) of hemagglutination-inhibiting antibodies[16]. Antibodies were tested by the standard hemagglutination inhibition (HI) assay[16] The anti-NKp46 mAb 461-G1 (IgG1) was generated by immunizing mice with the NKp46-Ig fusion proteins. Hybridomas were made according to standard techniques.

Direct Binding Assay

Rosettes of HA from X31 (A/Aichi/2/68xpr/8/34) H3N2 influenza virus were prepared as follows: purified HA was dialyzed against PH 5.0/0.1M citric acid in PBS over night at 4° C. For the ELISA assay, plates were coated with 0.1 µg of HA rosettes O.N at 4° C. After 2 h of blocking on ice with 1% BSA in PBS, plates were washed (1% BSA in PBS/0.05%/Tween 20) and incubated O.N at 4° C. with 0.1 g of the fusion protein or BSA for background (final volume of 100 µl of 1% BSA in PBS/0.05%/Tween 20). The detection of the amount of bound protein was preformed using AP-conjugated second mAb following standard ELISA protocol.

Primers Used for Generating NKp44 and NKp44 Truncated Fusion Proteins

TABLE 1

Primer sequence

| | | |
|---|---|---|
| NKp44 KpnI | 5' GGCAGGGTACCCCAATCCAAGGCTCAGG TA 3' | SEQ ID NO:9 |
| NKp44 KpnI DSF | 5' GGCAGGGTACCCTCTCCAGCCTCTGCCT CC 3' | SEQ ID NO:10 |
| 44/46 end seq | 5' GCCGTCCACGTACCAGTTGAA 3' | SEQ ID NO:11 |
| NKp44 BamHI DLR | 5' AAGGATCCGCTGGAGATACCACCAG 3' | SEQ ID NO:12 |

Production and Purification of Fusion Proteins

The generation of NKp46-Ig, NKp44-Ig, NKp30-Ig, KIR2DL1-Ig, and CD99-Ig in COS cells was previously described[13-15]. To generate the NKp46D1-Ig and NKp46D2 truncated fusion proteins in COS cells residues 1-120 (D1) and 121-235 (D2) of the mature NKp46 protein were PCR amplified, and the PCR-generated fragments were cloned into a mammalian expression vector containing the Fc portion of human IgG1 as previously described[13-15]. In order to allow expression of NKp46D2-Ig, that lacks its original leader peptide sequence, a methionine start codon was added and the PCR-amplified fragment of NKp46D2 was cloned in frame with the leader peptide of CD5. Sequencing of the constructs revealed that all cDNAs were in frame with the human Fc genomic DNA and were identical to the reported sequences. COS-7 cells were transiently transfected with the plasmids containing cDNAs using FuGENE6 reagent (Roche Molecular Biochemicals, Indianapolis, Ind., USA) according to the manufacturer's instructions, and supernatants were collected and purified on a protein G column. SDS-PAGE analysis revealed that all Ig fusion proteins were approximately 95% pure and of the proper molecular mass.

The sequence encoding the extracellular portion of NKp44 (accession number NM-004828, residues 1-169 not including leader), were amplified by PCR from cDNA isolated from human NK clones (see Table 1—list of the primers). The corresponding PCR fragment, containing kozak sequence and leader sequence of CD5, was cloned into pcDNA 3.1-Ig vector encoding the CH2+CH3 regions of human IgG1 (4). The sequences for truncated fusion proteins, NKp44D-Ig (residues 1-111 not including leader) and NKp44LP-Ig (residues 109-169) were amplified by PCR from the NKp44-Ig-encoding plasmid and the corresponding PCR fragments, containing kozak sequence and leader sequence of CD5, were back-cloned into pcDNA 3.1-Ig vector. Sequencing of the constructs revealed that all cDNAs were in frame with the human Fc DNA and were identical to the reported sequences. CHO cells were transfected with these expression vectors and G418-selected clones were screened for highest protein production. Re-cloned high producer clones were grown in CHO-SFM II medium (Gibco-BRL, Paisley, UK) and supernatants were collected daily and purified on protein-G columns using FPLC. SDS-PAGE analysis revealed that all Ig fusion proteins were approximately 95% pure and of the proper molecular mass, and migrate as a single band on standard non-reduced SDS-PAGE gels.

Staining procedures of cells with the fusion proteins was preformed as described[13-15]. For the production of NKp46D2 in CHO cells, the NKp46D2 fragment was amplified by PCR from NKp46D2-Ig expressing plasmid using primer with kozak sequences for high expression. These PCR fragments containing kozak sequence and leader sequence of CD5 were cloned into pcDNA 3.1-Ig vector. CHO cells were transfected with these expression vectors and were selected using G418 antibiotic. Selected clones were screened for highest protein production using ELISA. High producer clones were re-cloned and screened again for highest protein production. One clone was adapted for special serum-free medium (CHO-SFM II, Gibco) followed by optimization for growth in large-scale culture in T225 flasks or using spinner basket-Fibra cell (New Brunswick). Supernatant were collected daily and purified on protein-G columns using FPLC.

Treatment of Fusion Proteins with NA

Various fusion proteins were incubated with 0.015 U of insoluble neuraminidase attached to beaded agarose (N-5254; Sigma) or with PBS (control) for 1.5 h at 17° C. on a roller. SV and IV-infected, or non-infected cells were washed, and stained either with NA-treated or mock-treated Ig-fusion proteins, followed by PE-conjugated anti-human Fc. The integrity of the treated fusion proteins was assessed by SDS PAGE gel analysis.

The Generation of NKp46-Ig Point Mutations

The point mutations in the NKp46 protein T125A and N216A were generated by using PCR-based site directed mutagenesis approach as previously described[17]. The T225A and T225N mutations were generated by GenScript Corporation (Scotch Plains, N.J.). The existence of the mutations was verified by sequencing. All products were cloned in frame with human IgG1 as above. The production and the staining with the various fusion proteins were previously described[13-15]. All fusion proteins were routinely tested for degradation on SDS-PAGE gels.

Cytotoxicity Assays

The cytotoxic activity NK cells against various targets was assayed in 5-hr $^{35}$S-Met release assays, as described previously[13,14]. Re-directed lysis experiments of p815 cells were performed as previously described[13,14].

Flow Cytometry and Antibodies for NKp44

Cells were incubated with indicated mgs of the various fusion-Igs for 2 h at 4° C., washed and stained with FITC-conjugated-F(ab')$_2$-Goat-anti-human-IgG-Fcγ (109-096-098, Jackson ImmunoResearch, West Grove, Pa.). Staining and washing buffer consisted of 0.5% (w/v) BSA and 0.05% sodium azide in PBS. Staining of CHO and mutant CHO cells was carried with 2% FCS instead of BSA in the different buffers. Propidium iodide (PI) was added prior to reading for exclusion of dead cells. Flow cytometry was performed using a FACSCalibur flow cytometer (Becton Dickinson, Mountain View, Calif.). Data files were acquired and analyzed using BD CELLQuest™ 3.3 software. Fluorescence data was acquired using logarithmic amplification and reported fluorescence intensity units represent conversion of channel values according to the logarithmic scale (range 100 to 104). Results are shown either as staining histograms (X-axis represents fluorescence intensity and Y-axis represents cell counts) or as the geometric mean fluorescence intensity (MFI) of the stained populations. Geometric mean of the fluorescence intensities is recommended by BD for comparing relative fluorescence intensities between logarithmically-acquired samples. For most binding inhibition experiments, 20 mg of fusion-Ig were premixed with the GAG and added to cells for staining as above. In all experiments, each sample was stained twice in different wells. When results are presented as MFI, average MFI±SD of the duplicate staining is brought to show consistency of staining procedure. Human IgG1 (hIgG1) was purchased from Serotec, UK. HS4E4 control Ab was used as described previously[24].

Example 1

Viral HA is Directly Recognized by NKp46 and NKp44

To address whether the HA recognition by NKp46 and NKp44 is direct or if this interaction is only an initial step that mediates the binding of another ligand, a direct binding assay was employed. Because of the low dissociation constant for the binding of hemagglutinin to sialic acid (in the millimolar range), we could not detect any significant binding of NKp46 or NKp44 to a soluble bromelain-cleaved HA (BMH) in an ELISA assay. In order to overcome this problem we prepared rosettes of HA molecules by reducing the pH of a BMH solution to 5, as previously described[18]. Under these conditions, the BMH trimers form soluble aggregates called rosettes, containing about 6 to 10 BMH trimers. These rosettes do not change the affinity of HA to sialic acid, as has been previously demonstrated[19,20], but allow multivalent interaction in-vitro similarly to the virus binding of HA to its sialic acid receptors in-vivo. Such interactions could be monitored using BIAcore[20].

These rosettes were used to detect NKp46 and NKp44 interaction with HA in an ELISA assay.

Results: As shown in FIG. 1 both NKp46-Ig and NKp44-Ig strongly bound to the HA rosettes. This binding was specific to NKp46 and NKp44 since little or no binding was observed in the case of other Ig fusion proteins such as NKp30-Ig, which was used as a negative control. These results indicate that the HA recognition of NKp46 and NKp44 is direct and does not require the presence of other accessory or mediating molecules.

Example 2

The Primary Binding Site of HA on NKp46 is Located at the Second Domain

The extracellular region of NKp46 comprises two C2-type Ig-like domains while all the predicted sugar-carrying residues are located in the membrane proximal domain[6]. The inventors of the present invention have previously shown that the recognition of NKp46 by HA is dependent on the sialylation of the NKp46 receptor[13-15]. To determine that indeed the sialic acid residues of NKp46 are responsible for the interaction with viral HA, smaller versions of NKp46-Ig were prepared corresponding to single domains with their C-terminal fused to the Fc portion of human IgG1. The membrane distal domain was named NKp46D1 and the membrane proximal domain (including a stretch of amino acids that probably form a stem connecting the ectodomain with the transmembrane region) was named NKp46D2. The constructs were transiently transfected into COS-7 cells and secreted fusion proteins were purified on a protein-G column. The binding of each fusion protein to virally infected and uninfected 721.221 and 1106mel cells was analyzed.

As previously described[13-15], the binding of NKp46-Ig, but not NKp30-Ig, to 721.221 cells was considerably enhanced following SV infection and this binding was abolished by pre-incubation with anti-HA mAb 135.7 (FIG. 2). Remarkably, a similar pattern of increased binding to infected cells was also observed in the case of the truncated NKp46D2-Ig. Furthermore, this increased binding of NKp46D2-Ig was significantly blocked by mAb directed against HA (135.7), but not by the control mAbs TC-9A1, directed against the other glycoprotein of SV (the fusion protein) or by 12E7, directed against CD99. In contrast, the binding of NKp46D1-Ig to 721.221 was very weak and was not affected by infection or incubation with the various mAbs. Similar results were obtained when 1106mel cells were infected with IV. These observations indicate that the binding site of HA on NKp46 is located within the second domain of the receptor and that this domain is sufficient to mediate HA binding in a specific and efficient manner.

To extend the implications of these results, the binding of NKp46-Ig, NKp46D2-Ig and NKp46D1-Ig to 721.221 cells infected with different influenza viruses was examined (see Table 1). 721.221 cells were incubated overnight with or without influenza viruses that express different types of HA. Cells (50,000/well) were washed and stained with the various Ig fusion proteins (5 µg/well) followed by PE-conjugated goat anti human Fc. The level of infection was determined by staining with human sera derived from individuals immunized with a trivalent influenza vaccine. Median fluorescence intensity (MFI) numbers were rounded to the nearest whole number after subtracting background staining of the secondary antibody.

As previously reported[13-15], the binding of all lysis receptors to uninfected 721.221 cells was very low. This might be either because of low affinity interactions of the various NCR to their ligands or because the ligands for the various NCR are expressed in low levels on 721.221 cells. The highest binding to all infected cells was observed with NKp44-Ig. These might be because the NKp44 receptor carry more sugar residues compared with NKp46[6,8].

Results: in all the cases examined, the infection resulted with an increased parallel binding of both NKp46-Ig and NKp46D2-Ig, but did not effect the binding of NKp46D1-Ig or other control Ig-fusion proteins tested including NKp30 and CD99 (Table 2). The binding of NKp46D2 was consistently stronger than that of NKp46 probably because the smaller NKp46D2 protein is more stable. The differences in the intensity of the enhanced binding observed after infection with different viruses may be attributed to the differences in infection efficiency, determined by staining of infected cells with sera derived from individuals immunized with a trivalent influenza vaccine. Alternatively it is possible that the differences in the affinity of the specific HA molecule of the various viruses to NKp46 might be responsible for the different staining intensities. Infection of 1106mel cells with these viruses were similar to those obtained with 721.221 cells.

These findings demonstrate that the recognition of NKp46 and NKp44 by HA is a general phenomena with some degree of specificity and that in the case of NKp46, the binding is primarily mediated through the membrane proximal domain.

TABLE 2

The membrane proximal domain of NKp46 recognizes the HA of different viruses.

| | HA type | NKp44-Ig | NKp46-Ig | NKp46D2-Ig | NKp46D1-Ig | NKp30-Ig | CD99-Ig |
|---|---|---|---|---|---|---|---|
| uninfected | — | 7 | 3 | 4 | 2 | 2 | 0 |
| SV | HA-NA | 350 | 77 | 95 | 8 | 7 | 0.5 |
| Beijing | H1N1 | 128 | 44 | 77 | 7 | 4 | 0 |
| X-127 | H1N1 | 220 | 107 | 160 | 5 | 6 | 1 |
| New Caledonia | H1N1 | 518 | 315 | 420 | 5 | 10 | 0 |
| Sydney | H3N2 | 120 | 58 | 100 | 10 | 8 | 1 |
| Moscow | H3N2 | 24 | 20 | 50 | 8 | 8 | 0 |
| Yamanashi | B strain | 117 | 37 | 51 | 8 | 12 | 0 |

Example 3

The Sialylation of the Second Domain of NKp46 is Essential for the HA Recognition The common feature of all hemagglutinins is their ability to bind to oligosaccharides containing terminal sialic acid residues. In our previous work, we have shown that the recognition of viral HA by the lysis receptors NKp46 and NKp44 depends on the sialylation of these receptors[13-15]. NKp46 presumably displays two putative O-linked glycosylation sites at Thr125 and Thr225, and one N-linked glycosylation site at Asn216[6]. All the three putative sites are located within the second domain. Since our results clearly pointed the second domain of NKp46 to contain the primary binding site of influenza HAs, we next tested whether the sialic acid dependent nature of the interactions is also confined to the second domain.

Figure 3A:
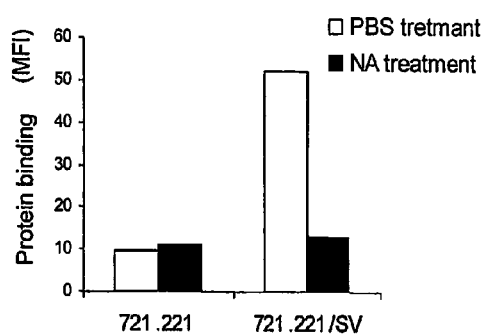
FIG. 3 demonstrates that the binding of the membrane proximal domain to viral HA is sialic acid dependent. NKp46D1-Ig (FIGS. 3b and 3c) or NKp46D2-Ig (FIGS. 3a and 3d) cells were treated with NA (filled bars) or with PBS as control (empty bars). SV- (FIGS. 3a and 3b) or IV- (FIGS. 3c and 3d) infected and uninfected 721,221 or 1106 mel cells, respectively, were washed and stained with either the PBS-treated or NA-treated fusion proteins followed by PE-conjugated goat antihuman Fc antibodies.
Figure 3B:
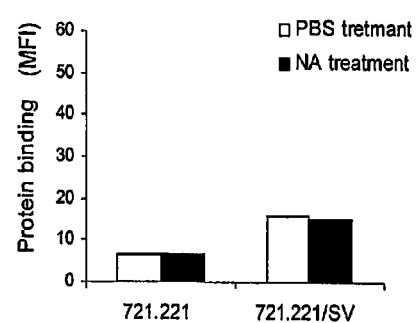
Figure 3B:
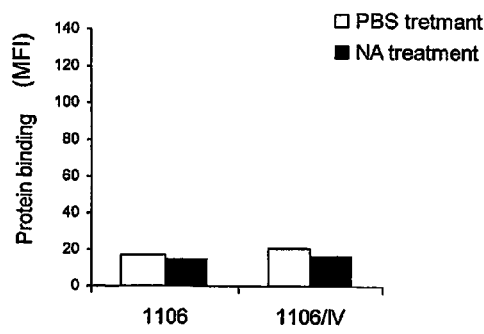
Figure 3D:
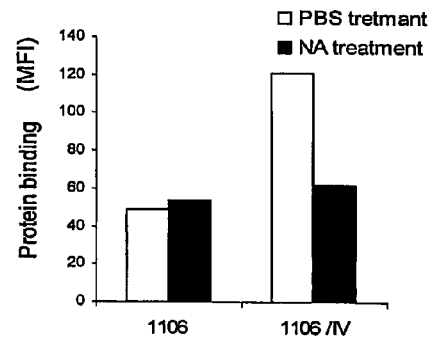

In order to answer this question we treated both NKp46D1-Ig and NKp46D2-Ig with bacterial neuraminidase (NA) before performing a binding assay on uninfected and IV or SV infected 1106mel and 721.221 cells, respectively. Indeed, treatment with NA completely abolished the enhanced binding of NKp46D2-Ig to SV-infected 721.221 (FIG. 3b) and IV-infected 1106mel (FIG. 3d) cells. Importantly however, the NA treatment did not affect the binding of NKp46D2-Ig to the uninfected cells suggesting that, in contrast to the binding to the viral HA, the binding to the cellular tumor ligand is not sialic acid dependent. As expected, 721.221 and 1106mel cells were only minimally recognized by NKp46D1 and treatment of NKp46D1-Ig with NA had no significant effect on its binding to either infected or uninfected cells (FIG. 3a, c). These results suggest that the sialylation of the second domain of NKp46 is indeed necessary for the binding to the viral HA, but is not involved in the recognition of tumor cells.

The two major linkages between sialic acid and the galactose residues of carbohydrate side chains are, Neu5Ac $\alpha(2,3)$-Gal and Neu5Ac $\alpha(2,6)$-Gal. Different HAs present different specificities for these linkages and in particular human influenza viruses preferentially bind the Neu5Ac $\alpha(2,6)$-Gal linkage[19]. To further explore the nature of the sialic acids of NKp46 that participate in the HA recognition we produced NKp46D2-Ig fusion protein in Chinese hamster ovary cells (CHO-D2-Ig) that expresses an impaired glycosylation pattern. CHO cells are wildly employed to produce glycosylated glycoproteins due to the high similarity between their glycosylation machinery to the human system. Notably however, CHO cells differ from human cells in the sialylation process since they lack a functional copy of the gene encoding $\alpha 2,6$-sialyltransferase[21]. As a result, while glycans of human origin carry terminal sialic acid residues in both $\alpha 2,3$- and $\alpha 2,6$-linkage, CHO glycoproteins carry only $\alpha 2,3$-terminal sialic acids.

We therefore compared the binding of the NKp46D2-Ig proteins produced either in CHO or in COS cells to 721.221 cells infected with mouse (SV) and various human influenza viruses were stained with both proteins.

Figure 4:
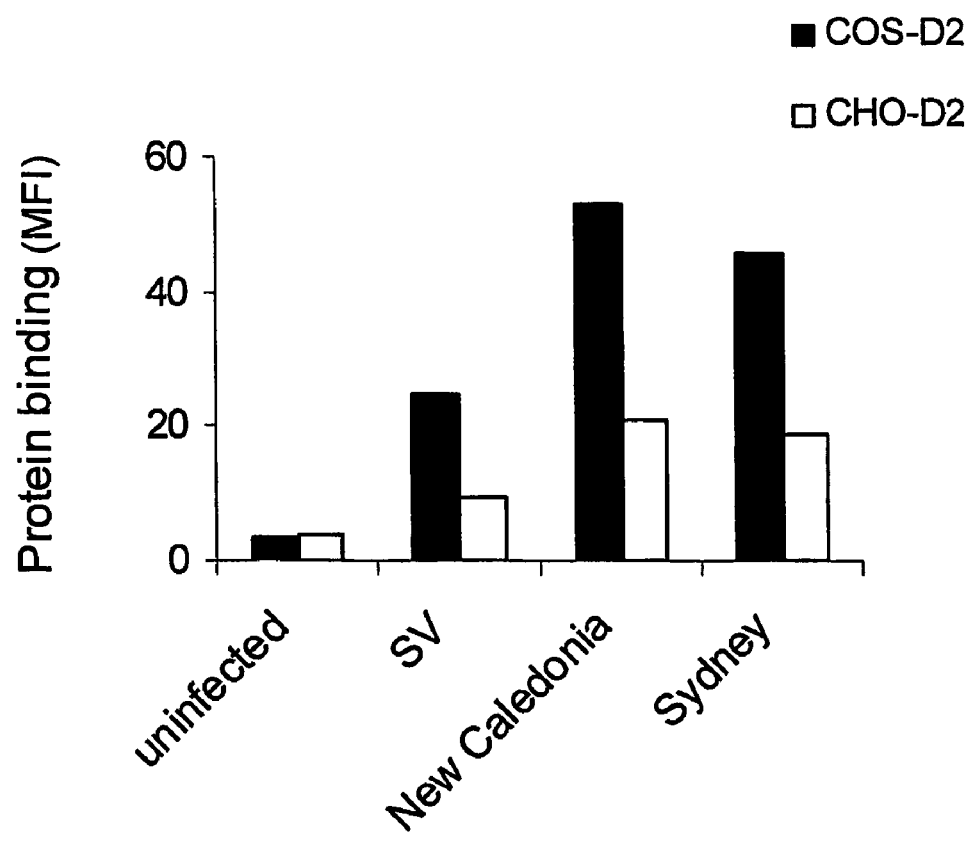
FIG. 4 demonstrates that impaired sialylation of NKp46D2-Ig in CHO cells significantly reduces HA binding.

Results: As shown in FIG. 4, the binding of CHO-D2-Ig to 721.221 infected cells was significantly weaker than the binding of the COS-produced NKp46D2-Ig protein. This observation stands in agreement with the binding specificity of HAs of human viruses and suggests that $\alpha 2,6$-terminal sialic acids modifications of NKp46 are important for its interaction with viral HAs. Similar results were obtained with other viruses or with 1106mel cells infected with the different viruses. Importantly, the integrity of CHO-D2 fusion protein was confirmed by SDS PAGE analysis and was supported by the fact that the binding of the CHO-D2-Ig to various tumor cell lines was similar to the binding of the COS-produced NKp46D2-Ig form.

Taken together, these observations support a predominant role of glycans expressed on the second domain of NKp46 that carry sialic acids of the $\alpha 2,6$-linkage in the recognition of human viral HAs. Notably however, the fact that in the absence of $\alpha 2,6$-terminal sialic acid, a reduced, yet significant enhanced binding was observed to infected cells suggest that there are probably other elements in NKp46 besides $\alpha 2,6$-terminal sialic acid moieties that participate in the interaction with HA. In addition, the similar binding of CHO- and COS-produced NKp46D2-Ig to various tumor cell lines indicates that sialic acids are not involved in the binding of NKp46 to tumor cells.

Example 4

Monoclonal Antibody Specifically Directed Against the Distal Membrane Domain of NKp46 does not Block NK-Mediated Lysis The above results suggest that the distal domain of NKp46 (D1) does not contain binding sites to HAs or tumor ligands of NKp46. However, these observations only relate to the binding properties of the domain and reveal nothing of other possible functional roles it may play in NKp46 activity. In addition, since all the binding assays were based on a truncated fusion protein form of the receptor, it was still possible that the lack of any binding observed was a result of loss of proper folding or weak interactions that could not be detected in immunostaining assays. Therefore, in order to study the possible involvement of the membrane distal domain of NKp46 in its function, we prepared a mAb directed specifically against the membrane distal domain of NKp46.

Figure 5D:
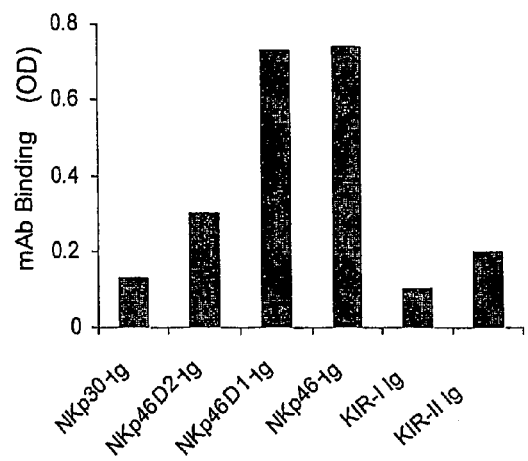
FIG. 5d shows the results of ELISA, in which the indicated immobilized fusion proteins were incubated with 461-G1 or no antibody, followed by incubation with HRP-conjugated rabbit antimouse IgG as secondary mAb.
Figure 5E:
FIG. 5e shows the results of SDS-PAGE and Western blot analysis of the fusion proteins NKp30-Ig (lane 1); NKp46D2-Ig (lane 2); NKp46D1-Ig (lane 4); NKp46-Ig (lane 5); KIR2DL1-Ig (lane 6), and the control low-protein medium (lane 3). The marker is indicated by M. Fusion proteins were analyzed with mAb 461-G1 and HRP-conjugated rabbit antimouse IgG.

To generate anti-NKp46 mAbs, we first used an immunization regimen based on NKp46-Ig protein emulsified in Freund adjuvant for both immunizations and boosts. Using ELISA assay, we screened spleen-derived B-cell hybridoma supernatants for increased binding to NKp46-Ig as compared to NKp30-Ig. Positive hybridomas were cloned and re-cloned to achieve stability. One hybridoma, named 461-G1, was stable and the secreted mAb was tested on different fusion proteins and cell lines. FIG. 5a-c—FACS staining experiments. NK cells (NK line), BW and BW transfected with NKp46 (BW/NKp46) were incubated with or without 0.5 µg 461-G1 mAb (black line) or control 12E7 mAb (grey histogram). 461-G1 recognized BW cells transfected with NKp46[13] and NK cells, but not BW cell lines or all other none NK cells that were tested. To further analyze the NKp46 domain to which 461-G1 binds, we performed ELISA assays comparing NKp46D1-Ig, NKp46D2-Ig, and NKp46-Ig and other Ig fusion proteins. FIG. 5d-ELISA plates were coated with 2 µg/ml of fusion proteins NKp30-Ig, NKp46D2-Ig, NKp46-D1-Ig, NKp46-Ig, KIR2DL1-Ig, KIRD12-Ig. Fusion proteins were incubated with no antibody or with 46.1-G1 for 1 h on ice. HRP conjugated rabbit-anti mouse IgG diluted 1:2500 was used as second Ab. PBS was used as negative control. Results showed that 461-G1 specifically recognized NKp46-D1-Ig and NKp46-Ig whereas only background recognition was observed with NKp46-D2-Ig or the other Ig fusion proteins tested.

FIG. 5e—10 µg of indicated proteins: NKp30-Ig (1), NKp46D2-Ig (2), NKp46D1-Ig (4), NKp46-Ig (5), KIR2DL1-Ig (6) and the control low protein medium (LPM, 3) were analyzed on SDS-PAGE electrophoresis. Western blot analysis showed similar results and 461-G1 recognized the NKp46-Ig and the NKp46D1-Ig only. Thus, 461-G1 specifically recognizes the membrane distal domain of NKp46.

Figure 5F:
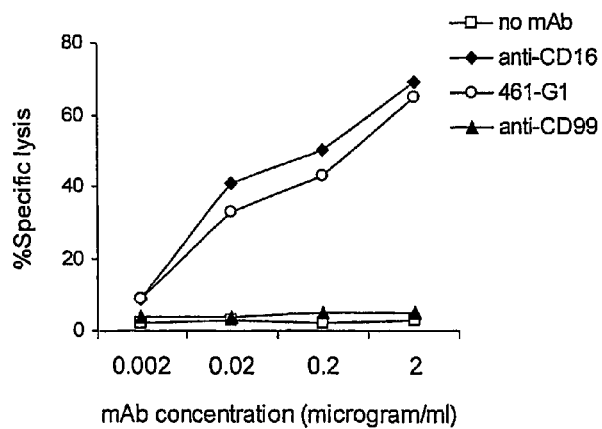
FIG. 5f shows the results of $^{35}$S-labeled cells incubated with no antibody (□), anti-CD16 mAb (B73.1.1; ♦), anti-NKp46 mAb (461-G1; ○) or anti-CD99 mAb (12E7; ▲), followed by addition of NK cells in effector to target ratio (E/T) of 3:1.

FIG. 5f—Redirected lysis experiment. $^{35}$S-labeled P815 cells were incubated either with no mAb or with the anti-CD16 mAb (B73.1.1), anti-NKp46 mAb (461-G1) or anti-CD99 mAb (12E7) for 1 hour on ice. NK cells were next added in effector to target ration (E:T) of 3:1. As previously reported with regard to other anti-NKp46 mAb[13-15] ligation of NKp46 on the surface of NK cells by 461-G1 mAb activated the redirected killing assay of the FcγR$^+$ P815 murine target cells, in a manner similar to that observed with the anti CD16 mAb (FIG. 5d).

The above results showed that the recognition of infected cells is confined to the membrane proximal domain. We have previously demonstrated an efficient blocking of NK cells cytotoxicity against influenza infected cells using anti-NKp46 serum[13]. In addition other anti-NKp46 mAb were shown to block the killing of various tumor targets[5-7,9].

Figure 5G:
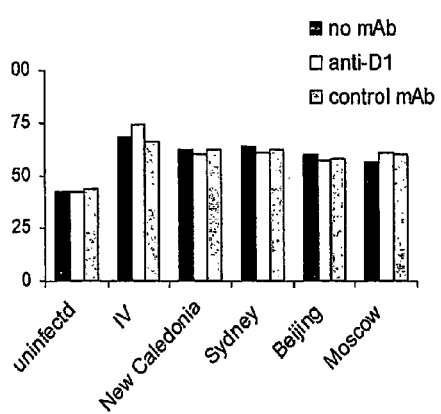
FIG. 5g shows the results of pre-incubating NK cells with the indicated mAbs, followed by incubation with either uninfected 1106 mel cells or 1106 mel cells infected with the indicated influenza strains, at E/T of 20:1.

FIG. 5g—NK killing assay with infected cells. NK cells were pre incubated with the indicated mAb for 1 h on ice, washed and incubated with either uninfected 1106mel or 1106mel infected with various influenzas as indicated. Pre-incubation of NK cells with 461-G1 mAb did not block the lysis of the melanoma cell line 1106mel before or after infection with various influenza viruses. Similarly, this mAb did not block the killing of other tumor lines tested including 721.221 or Hela cells.

Thus, the membrane distal domain of NKp46 is probably not involved in the recognition of tumor and virus-infected cells.

Example 5

The Sugar-Modification of Thr225 of NKp46 is Important for the HA Recognition

The molecular mechanism controlling the specific recognition of HAs by NKp46 is somewhat enigmatic. The difficulty is intensified in light of our above observation demonstrating the involvement of sialic acid residues that are expressed on NKp46 and are crucial for the HA recognition since other NK receptors that are also heavily glycosyated, such as NKp30-Ig, KIR1-Ig or CD99-Ig do not bind HAs[13-15] (Table 2).

Figure 6:
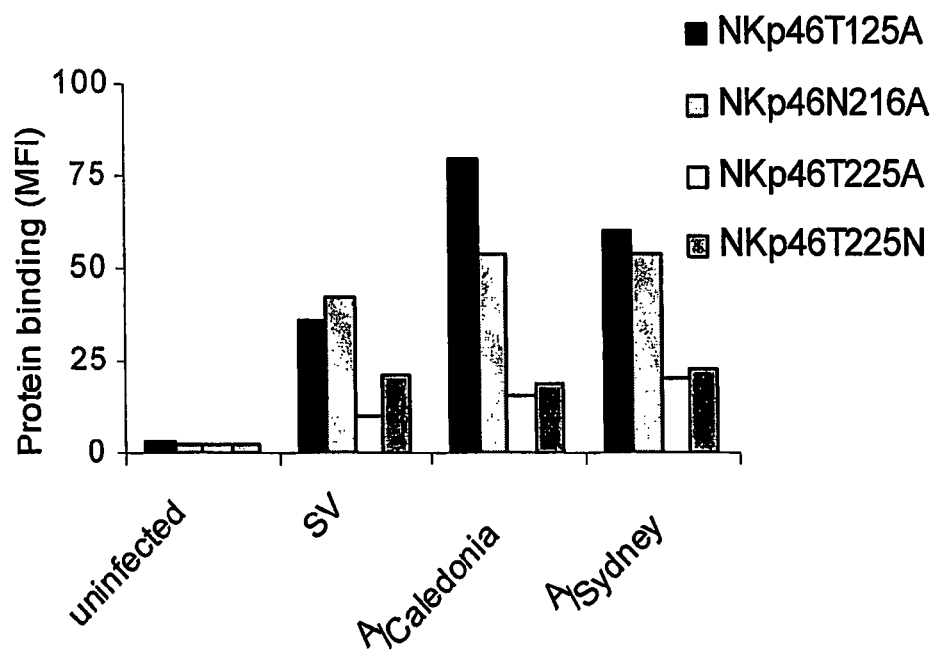
FIG. 6 demonstrates that the sialylation of Thr225 of NKp46 is important for the HA recognition.

To determine the sugar carrying residue that is important for the HA recognition, we performed site directed mutagenesis in the three residues that are predicted to carry the glycan modifications, produced the fusion proteins in COS cells as above and tested their binding to 721.221 cells infected with different influenza viruses. Substitution of Thr125 or Asn216 with Alanine (NKp46T125A and NKp46N216A, respectively) had no significant effect on the increased binding to infected cells (FIG. 6). Importantly, when Thr225 was substituted with Alanine a sharp decrease in the enhanced binding to the infected cells was observed (FIG. 6). Similar results were obtained when 1106mel cells were infected with the various influenzas. Thus, Thr225 of NKp46 is crucial to the binding of HA.

It is possible that the substitution of Thr225 with Alanine abolished an important glycosylation that is dominantly involved in the HA recognition. Alternatively, it may be that the Threonine residue is directly involved in the HA recognition. To distinguish between these two possibilities we replaced Threonine 225 with the closely related amino acid Asparagine (NKp46T225N). The reason why we preferred to replace Threonine with Asparagine and not with Serine that shares greater resemblance to Threonine is because Serine can potentially carry O-glycosylations in this location, while Asparagine can not. As shown in FIG. 6, expression of Asparagine instead of Threonine at position 225 did not restore the enhanced binding to infected cells, but instead was similar to the binding of NKp46T225A.

It is clear that the interaction between NKp46 and HA is not restricted to one amino acid only and other amino acid residues also contribute to the enhanced recognition of HA following infection. Indeed, the abolishment of the enhancement, resulting from Thr to Ala or Asn substitution was not complete (FIG. 6). Unfortunately, a NKp46 mutant in which all the predicted glycosylated residues were replaced by Alanine was also generated but, despite several attempts, could not be expressed in cells and therefore could not be tested.

In light of these observations, it is less likely that Thr225 is directly involved in the interaction with viral HA. Instead, this residue probably carries a critical glycosylation that is crucial, although not exclusive, for the recognition of HA.

Example 6

The Identification of the Binding Site of NKp46 to Tumor Ligands

As mentioned above, the important role of NK cells in anti tumor defense mechanisms is largely mediated through the NK lysis receptors. The NKp46 receptor, which is consistently expressed on NK cells, is thought to be the major lysis receptor involved in the killing of transformed cells[22,23]. However, since no specific tumor ligand for any of the lysis receptors has been identified yet, very little is known about the interactions between NKp46 and its tumor antigen ligand.

Figure 7:
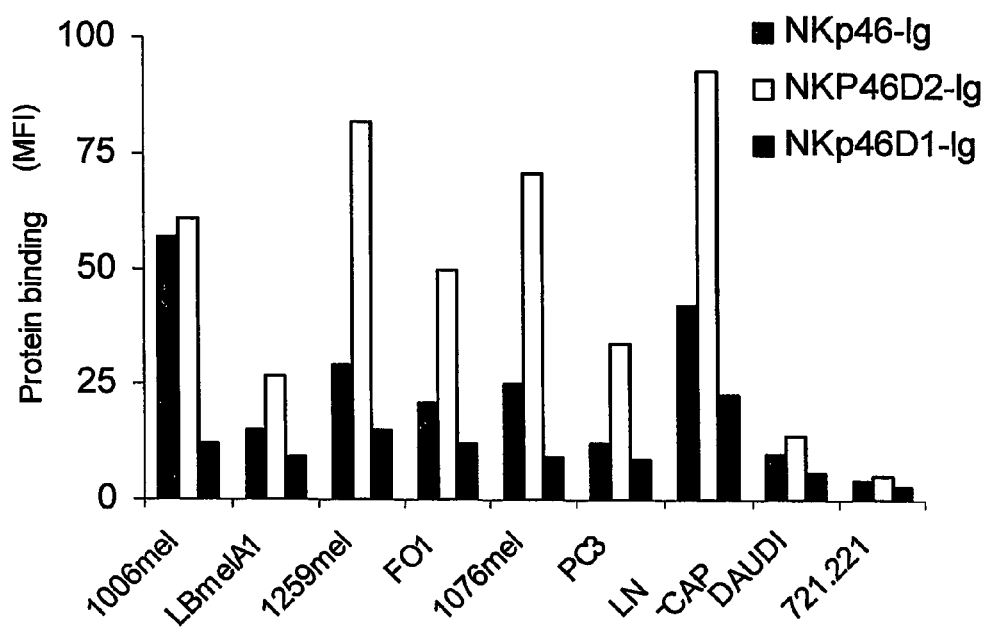
FIG. 7 demonstrates that the recognition of tumor cells by NKp46 is confined to the proximal membrane domain.
Figure 8A:
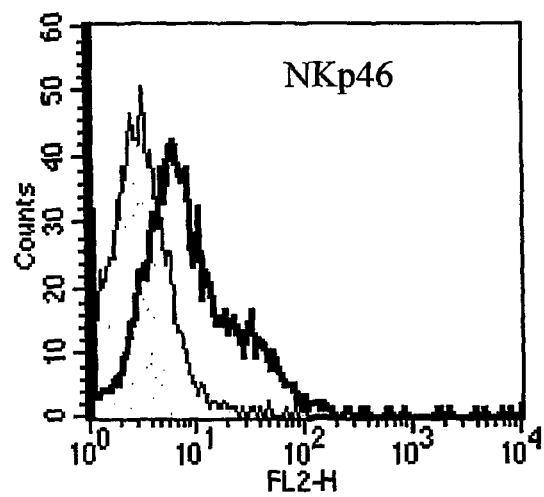
FIG. 8 demonstrates that amino acid residue Thr225 of NKp46 is crucial for the recognition of tumor cells by NKp46. 1106 mel cells were stained with the wild-type NKp46-Ig (FIG. 8a) or with the sugar-mutated forms NKp46T125A (FIG. 8b), NKp46N216A (FIG. 8c)., NKp46T225A (FIG. 8d), or NKp46T225N (FIG. 8e), followed by PE-conjugated goat antihuman Fc.
Figure 8B:
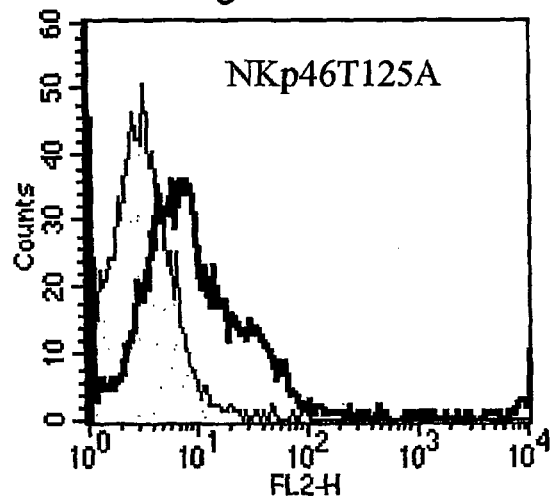
Figure 8C:
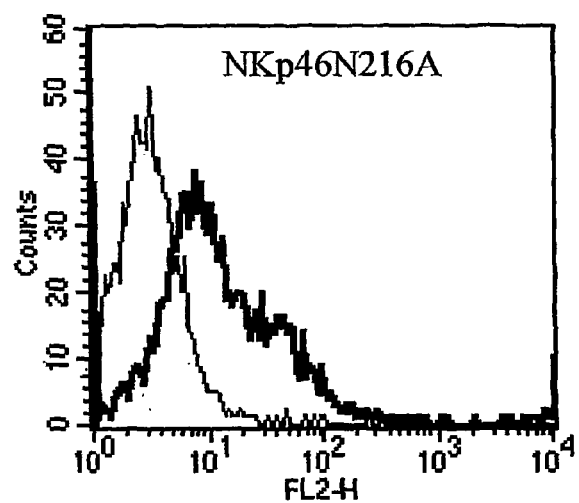
Figure 8D:
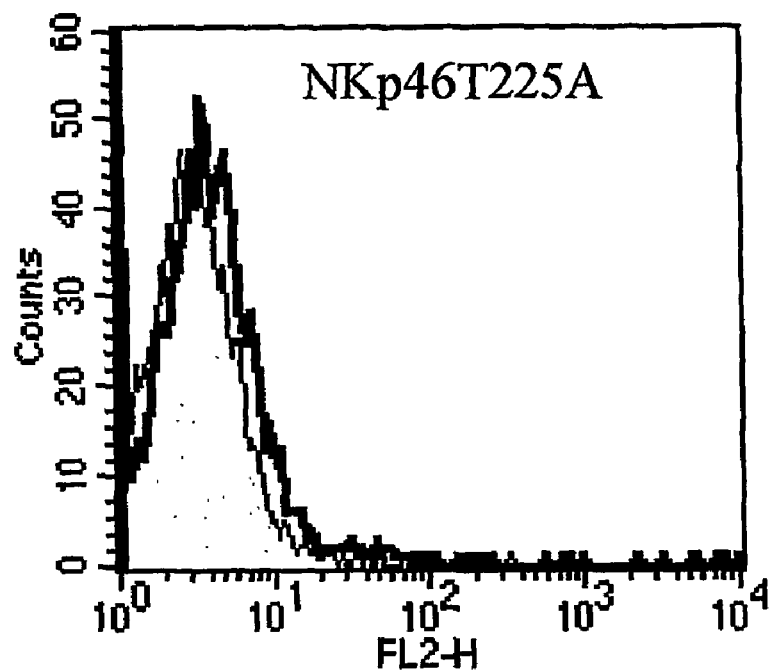
Figure 8E:
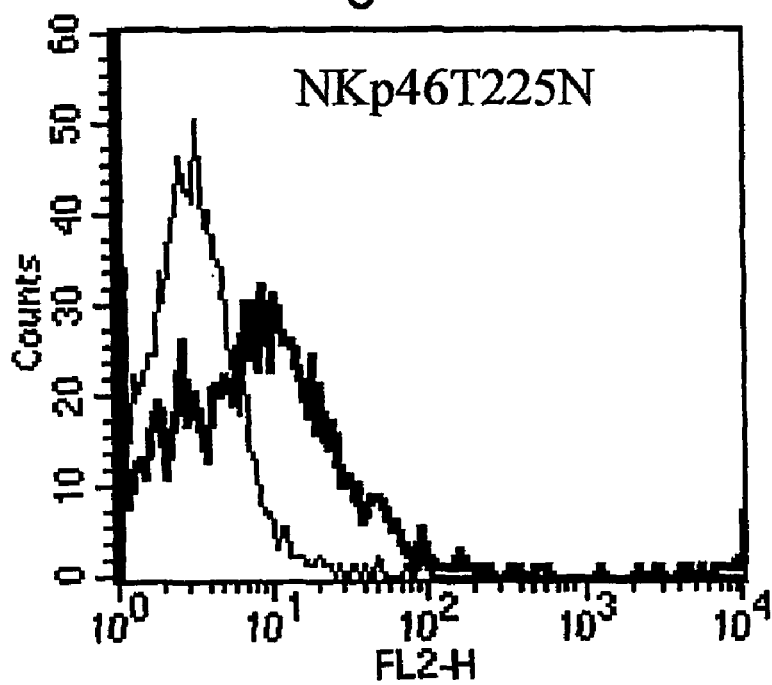
Figure 10B:
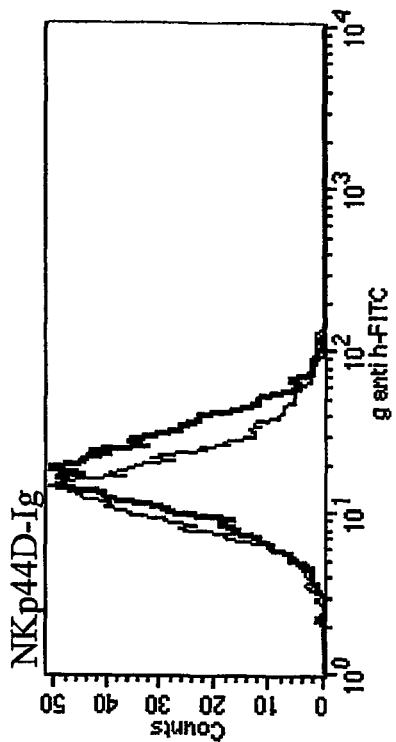
FIG. 10 demonstrates the binding of NKp44-Ig, NKp44D-Ig and NKp44LP-Ig to viral-infected cells. Uninfected 1106 mel cells (thick black line) and 1106 mel cellsinfected with IV (thin black line) were incubated with fusion proteins NKp44-Ig (FIG. 10a), NKp44D-Ig (FIG. 10b), NKp44LP-Ig (FIG. 10c), or with secondary antibody as control (FIG. 10d), followed by staining with FITC-anti-Fc secondary antibody.
Figure 10D:
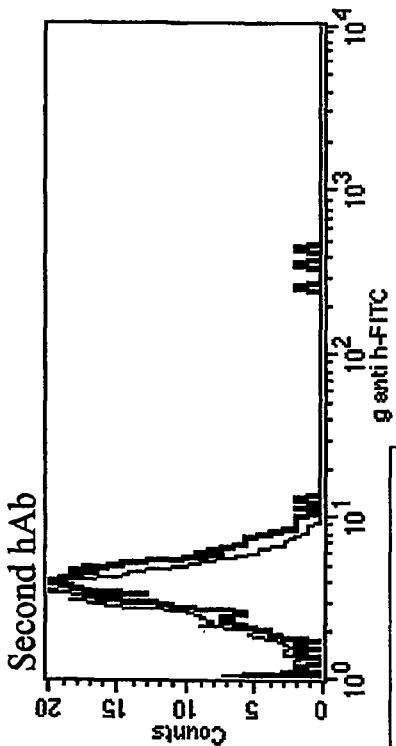
Figure 10A:
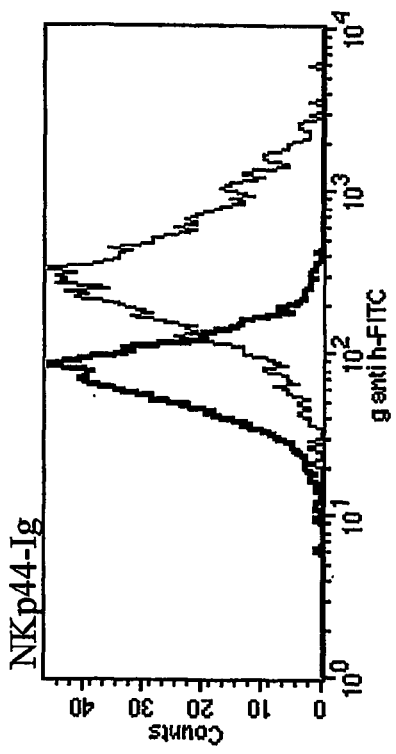
Figure 10C:
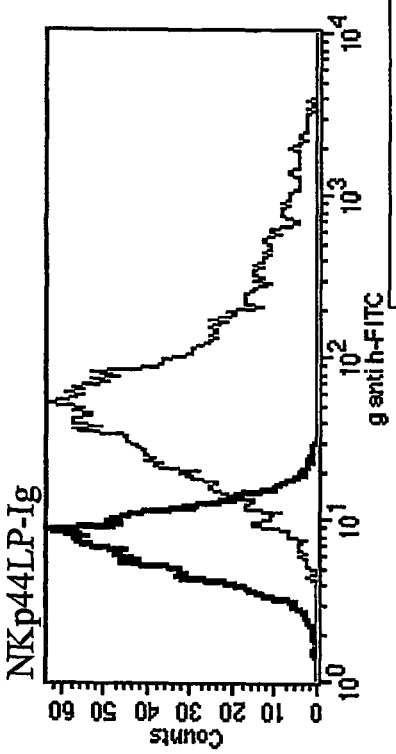

To gain better understanding of tumor recognition by NKp46, we immunostained a number of different tumor lines including melanomas, carcinomas and EBV transformed B cells with the intact NKp46 protein and the fragmented NKp46D2- and NKp46D1-Ig fusion proteins. The various tumor lines were recognized by NKp46 and NKp46D2 to various degree (FIG. 7), suggesting the tumor ligands for the NKp46 receptors are expressed in different levels on various tumors. In general and as reported above, the highest binding was observed with the NKp46D2. Importantly, all the different tumors tested were stained by the second domain of NKp46 in correlation with the staining by the full NKp46-Ig, while weak or no staining was observed by the NKp46D1-Ig protein (FIG. 7). Thus, similarly to the binding to viral HA and in agreement with the inability of 461-G1 to block tumor cells killing (FIG. 5) the ability of NKp46 to recognize many different tumor cells is mediated via the second domain of the receptor.

As mentioned above, impairment of the expression of sialic acids residues in NKp46, either by NA treatment or CHO production, did not affect its binding to tumor cells, suggesting no involvement of carbohydrate moieties of NKp46 in tumor cells recognition. To support this conclusion we next tested the binding of the various glycosylation mutants to tumor cells. To our surprise, NKp46-Ig expressing the point mutation of Thr225 to Alanine completely lost its binding to 1106mel (FIG. 8) and other tumor cells tested. Remarkably, binding was fully restored when Thr225 was replaced with its closely resembled amino acid Asparagine. Mutations in the other two glycosylation sites had no effect on the binding.

In conclusion, our findings identify Thr225 as an essential amino acid involved in the interaction of NKp46 with tumor and virus-infected cells and support a sialic acid independent interaction between NKp46 and its tumor ligand. This places Thr225 as a central amino acid important to both viral HA as well as tumor ligand recognition.

Example 7

Titration of NKp44-Ig, NKp44D-Ie and NKp44LP-Ig Binding to Tumor Cells

Titrated amounts of fusion-Ig were added to tumor cells for 2 h at 4° C. (100 µl total volume). After incubation, cells were washed and incubated with FITC-conjugated-goat antihuman-Fc second antibody. PI was added to exclude dead cells. FIG. 9a: Graph: staining of PC-3 cells. Results are presented as mean fluorescence intensity (MFI, see methods) after subtraction of background staining with second antibody (MFI=4 for background staining). FIG. 9b: primary FACS histogram overlay showing staining of HeLa cells with 20 µg fusion-Igs. Results are from 1 representative experiment of 2 (9a) and 5 (9b). For the graph, results are the average of 2 different samples assayed in the same experiment. Bars, ±SD (of the duplicate, indicating the consistency of the staining procedure).

Results: As demonstrated in FIG. 9, NKp44LP-Ig showed none to negligible tumor binding, while NKp44D-Ig recognition was one log less as compared to the high recognition of these tumors by NKp44-Ig. Binding of NKp44-Ig to PC3 cells maximize at 20 µg (100 µg 1 ml) while binding of NKp44D-Ig reach to plateau at 40 µg (200 µg/ml).

Example 8

Binding of NKp44-Ig, NKp44D-Ig and NKp44LP-Ig Binding to IV-Infected Cells

1106mel cells ($10^6$/ml) were incubated overnight with 1000 u/ml of IV. Cells (infected or uninfected) were washed, incubated with fusion-Igs, and stained with FITC-anti-Fc second antibody. PI was added to exclude dead cells. Primary FACS histogram overlays: staining with NKp44-Ig (A), NKp44D-Ig (B) and NKp44LP-Ig (C). Results are from 1 representative experiment of 3.

Results: As demonstrated in FIG. 10, NKp44LP contain all the glycosylations sites predicated for NKp44 (13 O-sites and 2 N-sites) while NKp44D has none. NKp44LP did not bind to tumors, but did efficiently bind to the hemagglutinin expressed on viral-infected cells, while NKp44D does not manifest any enhanced binding after virus infection. These results raise the possibility of the use of over-glycosylated peptides (LP is 61 amino acids) as a tool to recognize viruses or virus-infected cells expressing hemagglutinins on the virus envelope or cell membrane.

It will be appreciated by a person skilled in the art that the present invention is not limited by what has been particularly shown and described hereinabove. Rather, the scope of the invention is defined by the claims that follow.

REFERENCES

1. Biassoni R, Cantoni C, Pende D, Sivori S, Parolini S, Vitale M, Bottino C, Moretta A. Human natural killer cell receptors and co-receptors. Immunol Rev. 2001; 181:203-214

2. Ljunggren H G, Karre K. In search of the 'missing self': MHC molecules and NK cell recognition. Immunol Today. 1990; 11:237-244

3. Markel G, Wolf D, Hanna J, Gazit R, Goldman-Wohl D, Lavy Y, Yagel S, Mandelboim O. Pivotal role of CEACAM1 protein in the inhibition of activated decidual lymphocyte functions. J Clin Invest. 2002; 110:943-953

4. Sivori S, Vitale M, Morelli L, Sanseverino L, Augugliaro R, Bottino C, Moretta L, Moretta A. p 46, a novel natural killer cell-specific surface molecule that mediates cell activation. J Exp Med. 1997; 186:1129-1136

5. Pende D, Parolini S, Pessino A, Sivori S, Augugliaro R, Morelli L, Marcenaro E, Accame L, Malaspina A, Biassoni R, Bottino C, Moretta L, Moretta A. Identification and molecular characterization of NKp30, a novel triggering receptor involved in natural cytotoxicity mediated by human natural killer cells. J Exp Med. 1999; 190:1505-1516

6. Pessino A, Sivori S, Bottino C, Malaspina A, Morelli L, Moretta L, Biassoni R, Moretta A. Molecular cloning of NKp46: a novel member of the immunoglobulin superfamily involved in triggering of natural cytotoxicity. J Exp Med. 1998; 188:953-960

7. Vitale M, Bottino C, Sivori S, Sanseverino L, Castriconi R, Marcenaro E, Augugliaro R, Moretta L, Moretta A. NKp44, a novel triggering surface molecule specifically expressed by activated natural killer cells, is involved in non-major histocompatibility complex-restricted tumor cell lysis. J Exp Med. 1998; 187:2065-2072

8. Cantoni C, Bottino C, Vitale M, Pessino A, Augugliaro R, Malaspina A, Parolini S, Moretta L, Moretta A, Biassoni R. NKp44, a triggering receptor involved in tumor cell lysis by activated human natural killer cells, is a novel member of the immunoglobulin superfamily. J Exp Med. 1999; 189:787-796

9. Sivori S, Pende D, Bottino C, Marcenaro E, Pessino A, Biassoni R, Moretta L, Moretta A. NKp46 is the major triggering receptor involved in the natural cytotoxicity of fresh or cultured human NK cells. Correlation between surface density of NKp46 and natural cytotoxicity against autologous, allogeneic or xenogeneic target cells. Eur J Immunol. 1999; 29:1656-1666

10. Costello R T, Sivori S, Marcenaro E, Lafage-Pochitaloff M, Mozziconacci M J, Reviron D, Gastaut J A, Pende D, Olive D, Moretta A. Defective expression and function of natural killer cell-triggering receptors in patients with acute myeloid leukemia. Blood. 2002; 99:3661-3667

11. Vankayalapati R, Wizel B, Weis S E, Safi H, Lakey D L, Mandelboim O, Samten B, Porgador A, Barnes P F. The NKp46 receptor contributes to NK cell lysis of mononuclear phagocytes infected with an intracellular bacterium. J Immunol. 2002; 168:3451-3457

12. Biron C A, Nguyen K B, Pien G C, Cousens L P, Salazar-Mather T P. Natural killer cells in antiviral defense: function and regulation by innate cytokines. Annu Rev Immunol. 1999; 17:189-220

13. Mandelboim O, Lieberman N, Lev M, Paul L, Amon T I, Bushkin Y, Davis D M, Strominger J L, Yewdell J W, Porgador A. Recognition of haemagglutinins on virus-infected cells by NKp46 activates lysis by human NK cells. Nature. 2001; 409:1055-1060

14. Amon T I, Lev M, Katz G, Chernobrov Y, Porgador A, Mandelboim O. Recognition of viral hemagglutinins by NKp44 but not by NKp30. Eur J Immunol. 2001; 31:2680-2689

15. Amon T I, Achdout H, Lieberman N, Gazit R, Gonen-Gross T, Katz G, Bar-Ilan A, Bloushtain N, Lev M, Joseph A, Kedar E, Porgador A, Mandelboim O. The mechanisms controlling the recognition of tumor and virus infected cells by NKp46. Blood. 2004; 103:664-672

16. Ben-Yehuda A, Joseph A, Zeira E, Even-Chen S, Louria-Hayon I, Babai I, Zakay-Rones Z, Greenbaum E, Barenholz Y, Kedar E. Immunogenicity and safety of a novel liposomal influenza subunit vaccine (INFLUSOME-VAC) in young adults. J Med Virol. 2003; 69:560-567

17. Mandelboim O, Malik P, Davis D M, Jo C H, Boyson J E, Strominger J L. Human CD16 as a lysis receptor mediating direct natural killer cell cytotoxicity. Proc Natl Acad Sci USA. 1999; 96:5640-5644

18. Skehel J J, Bayley P M, Brown E B, Martin S R, Waterfield M D, White J M, Wilson I A, Wiley D C. Changes in the conformation of influenza virus hemagglutinin at the pH optimum of virus-mediated membrane fusion. Proc Natl Acad Sci USA. 1982; 79:968-972

19. Skehel J J, Wiley D C. Receptor binding and membrane fusion in virus entry: the influenza hemagglutinin. Annu Rev Biochem. 2000; 69:531-569

20. Takemoto D K, Skehel J J, Wiley D C. A surface plasmon resonance assay for the binding of influenza virus hemagglutinin to its sialic acid receptor. Virology. 1996; 217: 452-458

21. Lee E U, Roth J, Paulson J C. Alteration of terminal glycosylation sequences on N-linked oligosaccharides of Chinese hamster ovary cells by expression of beta-galactoside alpha 2,6-sialyltransferase. J Biol Chem. 1989; 264: 13848-13855

22. Moretta L, Bottino C, Pende D, Mingari M C, Biassoni R, Moretta A. Human natural killer cells: their origin, receptors and function. Eur J Immunol. 2002; 32:1205-1211

23. Long E O. Tumor cell recognition by natural killer cells. Semin Cancer Biol. 2002; 12:57-61

24. Dennissen, M. A., G. J. Jenniskens, M. Pieffers, E. M. Versteeg, M. Petitou, J. H. Veerkamp, and T. H. van Kuppevelt. 2002. Large, tissue-regulated domain diversity of heparan sulfates demonstrated by phage display antibodies. *J Biol Chem* 277:10982.

The invention claimed is:

1. An isolated peptide fragment of the natural cytotoxicity receptor NKp46, wherein the peptide fragment comprises a peptide of the D2 domain of the NKp46 receptor that is 20-100 amino acid residues in length and wherein said peptide fragment exhibits at least one activity selected from binding to a viral infected cell or binding to a tumor cell.

2. The peptide fragment of claim 1 comprising at least one glycosylated residue.

3. The isolated peptide fragment of the human NKp46 receptor according to claim 1, the peptide having the ability to bind to target cells selected from viral-infected cells and tumor cells, with the proviso that said peptide is other than SEQ ID NOs: 1 and 2.

4. The peptide fragment of claim 3 wherein the target cell is of a warm-blooded vertebrate.

5. The peptide fragment of claim 4 wherein the target cell is of human origin.

6. The peptide fragment of claim 3 comprising a minimal epitope of NKp46 receptor having ability to bind to viral-infected cells.

7. The peptide fragment of claim 6 comprising a glycosylated residue corresponding to threonine at position 225 of isoform a of the human NKp46 receptor.

8. The peptide of claim 6 wherein the glycosylated residue comprises sialic acid.

9. The peptide fragment of claim 3 comprising from about 25 to 75 amino acids.

10. The peptide fragment of claim 3 comprising from about 30 to 60 amino acids.

11. A fusion protein comprising an isolated peptide fragment of the natural cytotoxicity receptor NKp46, and further comprising a molecule selected from an immunoglobulin (Ig) molecule or a fragment thereof, and a cytotoxic substance; wherein the peptide fragment comprises a peptide of the D2 domain of the NKp46 receptor that is 20-100 amino acid residues in length; wherein said fusion protein comprising said peptide fragment exhibits at least one activity selected from binding to a viral infected cell or binding to a tumor cell; and wherein said fusion protein is other than the fusion proteins of SEQ ID NOs:13-16.

12. The fusion protein of claim 11 manufactured by recombinant DNA technology or chemical synthesis.

13. The fusion protein of claim 11 comprising the peptide fragment covalently conjugated to a molecule selected from an immunoglobulin (Ig) molecule or a fragment thereof, and a cytotoxic substance.

14. The fusion protein of claim 13 wherein the peptide fragment is covalently conjugated to the Fc fragment of said immunoglobulin molecule.

15. A variant polypeptide of the natural cytotoxicity receptor NKp46, the variant comprising a single amino acid substitution in an epitope required for recognition of viral-infected cells or tumor cells, wherein the epitope is in the proximal domain of the NKp46 receptor a (SEQ ID NO:1), and wherein the single amino acid substitution is at an amino acid residue selected from the group consisting of Threonine 125, Threonine 225 and Asparagine 216.

16. The variant polypeptide of claim 15, wherein the single amino acid substitution is selected from the group consisting of: Threonine 225 replaced by an amino acid residue selected from the group consisting of Serine, Alanine and Asparagine; Threonine 125 replaced by Alanine, and Asparagine 216 replaced by Alanine.

17. The variant polypeptide of claim 15, wherein the amino acid substitution is at a glycosylation site within the proximal domain of the NKp46 receptor.

18. The variant polypeptide of claim 15, comprising at least one glycosylated residue.

19. The variant polypeptide of claim 18, wherein the glycosylated residue comprises sialic acid.

20. The variant polypeptide of claim 15, wherein said polypeptide exhibits at least one activity selected from binding to a viral infected cell and binding to a tumor cell.

21. The variant polypeptide of claim 20, having the ability to bind to viral-infected cells.

22. The variant polypeptide of claim 20, having the ability to bind to tumor cells.

23. The variant polypeptide of claim 20, comprising a glycosylated Threonine residue corresponding to Threonine 225 of isoform a of the human NKp46 receptor.

24. The variant polypeptide of claim 23, wherein the glycosylated residue comprises sialic acid.

25. A fusion protein comprising the variant polypeptide of claim 15, and further comprising an immunoglobulin (Ig) molecule or a fragment thereof.

26. The fusion protein of claim 25, comprising the Fc fragment of said immunoglobulin molecule.

* * * * *

UNITED STATES PATENT AND TRADEMARK OFFICE
CERTIFICATE OF CORRECTION

| | | |
|---|---|---|
| PATENT NO. | : 7,825,085 B2 | Page 1 of 1 |
| APPLICATION NO. | : 10/562735 | |
| DATED | : November 2, 2010 | |
| INVENTOR(S) | : Mandelboim et al. | |

It is certified that error appears in the above-identified patent and that said Letters Patent is hereby corrected as shown below:

Title Page:
Item (75) Inventors, please correct the spelling "Lehavia" to -- Lehavim --.

Column 60:
Line 16 (claim 15), before "recognition" insert -- the --.

Signed and Sealed this
Twenty-fourth Day of April, 2012

David J. Kappos
*Director of the United States Patent and Trademark Office*